US009987385B2

(12) United States Patent
Bhaumik

(10) Patent No.: US 9,987,385 B2
(45) Date of Patent: Jun. 5, 2018

(54) INSTRUMENT REPROCESSOR AND INSTRUMENT REPROCESSING METHODS

(71) Applicant: Ethicon, Inc., Somerville, NJ (US)

(72) Inventor: Ujjal Bhaumik, Yorba Linda, CA (US)

(73) Assignee: ETHICON, INC., Somerville, NJ (US)

( * ) Notice: Subject to any disclaimer, the term of this patent is extended or adjusted under 35 U.S.C. 154(b) by 517 days.

(21) Appl. No.: 14/533,789

(22) Filed: Nov. 5, 2014

(65) Prior Publication Data

US 2015/0059806 A1   Mar. 5, 2015

Related U.S. Application Data

(62) Division of application No. 13/278,874, filed on Oct. 21, 2011, now Pat. No. 8,920,574.

(51) Int. Cl.

| | |
|---|---|
| *A61B 90/70* | (2016.01) |
| *A61B 1/12* | (2006.01) |
| *A61L 2/24* | (2006.01) |
| *A61L 2/18* | (2006.01) |
| *B08B 3/04* | (2006.01) |

(Continued)

(52) U.S. Cl.
CPC .............. *A61L 2/24* (2013.01); *A61B 1/123* (2013.01); *A61B 1/125* (2013.01); *A61B 90/70* (2016.02); *A61L 2/18* (2013.01); *B08B 3/04* (2013.01); *B08B 9/00* (2013.01); *G05D 16/2013* (2013.01); *A61B 2090/701* (2016.02); *Y10T 137/7761* (2015.04); *Y10T 137/8601* (2015.04)

(58) Field of Classification Search
None
See application file for complete search history.

(56) References Cited

U.S. PATENT DOCUMENTS

| | | |
|---|---|---|
| 6,423,266 B1 | 7/2002 | Choperena et al. |
| 7,340,943 B2 | 3/2008 | Jackson et al. |
| | (Continued) | |

FOREIGN PATENT DOCUMENTS

| | | |
|---|---|---|
| CN | 1933768 A | 3/2007 |
| CN | 101795618 A | 8/2010 |
| | (Continued) | |

OTHER PUBLICATIONS

English Machine Translation of JP 2004-354126 A.*

*Primary Examiner* — Nicole Blan
(74) *Attorney, Agent, or Firm* — K&L Gates LLP

(57) ABSTRACT

An instrument reprocessor for cleaning, disinfecting, and/or sterilizing a medical instrument is disclosed. To reprocess instruments having one or more channels defined therein, the reprocessor can include one or more flow control systems configured to control a flow of fluid through each channel. In various embodiments, a flow control system can include a differential pressure sensor and a proportional valve for controlling the fluid flow in a channel. The reprocessor can also include, one, a fluid circulation pump which can be configured to supply the flow control systems with fluid and, two, a system for controlling the pressure of the fluid supplied to the flow control systems. The reprocessor can also include a system for supplying a metered amount of fluid to the fluid circulation system. The system can include a reservoir having a fluid height sensor to monitor the amount of fluid therein and a pump configured to supply the reservoir with fluid.

11 Claims, 18 Drawing Sheets

(51) Int. Cl.
*B08B 9/00* (2006.01)
*G05D 16/20* (2006.01)

(56) References Cited

U.S. PATENT DOCUMENTS

| | | | |
|---|---|---|---|
| 7,740,813 B2 | 6/2010 | Williams | |
| 7,824,608 B2 | 11/2010 | Kuroshima et al. | |
| 7,857,004 B2 | 12/2010 | Pearson | |
| 7,879,289 B2 | 2/2011 | Williams | |
| 8,591,668 B2 | 11/2013 | Pieroni et al. | |
| 8,758,519 B2 | 6/2014 | Waldmann et al. | |
| 8,920,574 B2 | 12/2014 | Bhaumik et al. | |
| 2002/0092547 A1* | 7/2002 | You | B08B 3/00 134/36 |
| 2005/0209507 A1 | 9/2005 | Suzuki et al. | |
| 2007/0154343 A1 | 7/2007 | Kral et al. | |
| 2009/0135868 A1 | 5/2009 | Ishibashi | |
| 2009/0220377 A1* | 9/2009 | Hasegawa | A61B 1/123 422/28 |
| 2011/0298209 A1 | 12/2011 | Nguyen et al. | |
| 2012/0007352 A1 | 1/2012 | Nguyen et al. | |
| 2013/0098407 A1 | 4/2013 | Perlman et al. | |

FOREIGN PATENT DOCUMENTS

| | | | | |
|---|---|---|---|---|
| EP | 0072257 A2 | 2/1983 | | |
| EP | 2407234 A1 | 1/2012 | | |
| EP | 1902735 B1 | 8/2012 | | |
| EP | 2576090 B1 | 10/2017 | | |
| JP | H08-238258 A | 9/1996 | | |
| JP | H11-514065 A | 11/1999 | | |
| JP | 2000-205052 A | 7/2000 | | |
| JP | 2004354126 A * | 12/2004 | | G05D 7/0635 |
| JP | 2006-314709 A | 11/2006 | | |
| JP | 2007-252251 A | 10/2007 | | |
| JP | 2010-0577520 A | 3/2010 | | |
| TW | 200413699 A | 8/2004 | | |
| TW | 200925560 A | 6/2009 | | |
| TW | 200938141 A | 9/2009 | | |
| TW | 200938979 A | 9/2009 | | |
| TW | 201034764 A | 10/2010 | | |

* cited by examiner

INSTRUMENT REPROCESSOR AND INSTRUMENT REPROCESSING METHODS

CROSS REFERENCE TO RELATED APPLICATIONS

The present application is a divisional application claiming priority under 35 U.S.C. § 120 to co-pending U.S. patent application Ser. No. 13/278,874, entitled "INSTRUMENT REPROCESSOR AND INSTRUMENT REPROCESSING METHODS," filed Oct. 21, 2011, the entire disclosure of which is incorporated by reference herein.

BACKGROUND i. Field of the Invention

The present invention generally relates to the reprocessing, cleaning, sterilizing, and/or decontamination of medical instruments.

ii. Description of the Related Art

In various circumstances, an endoscope can include an elongate portion, or tube, having a distal end which can be configured to be inserted into the body of a patient and, in addition, a plurality of channels extending through the elongate portion which can be configured to direct water, air, and/or any other suitable fluid into a surgical site. In some circumstances, one or more channels in an endoscope can be configured to guide a surgical instrument into the surgical site. In any event, an endoscope can further include a proximal end having inlets in fluid communication with the channels and, in addition, a control head section having one or more valves, and/or switches, configured to control the flow of fluid through the channels. In at least one circumstance, an endoscope can include an air channel, a water channel, and one or more valves within the control head configured to control the flow of air and water through the channels.

Decontamination systems can be used to reprocess previously-used medical devices, such as endoscopes, for example, such that the medical devices can be used again. A variety of decontamination systems exist for reprocessing endoscopes. In general, such systems may include at least one rinsing basin in which an endoscope that is to be cleaned and/or disinfected can be placed. The rinsing basin is commonly supported by a housing that supports a circulation system of lines, pumps and valves for the purpose of directing a cleaning and/or disinfecting agent into and/or onto an endoscope which has been placed in the basin. During the decontamination process, the channels within the endoscope can be evaluated in order to verify that the channels are unobstructed. In various embodiments, the circulation system can be fluidly coupled to the endoscope channels by connectors which releasably engage ports which can define the ends of the channels. Such connectors can achieve a fluid-tight seal while attached to the endoscope, yet they can be easily releasable at the conclusion of the decontamination process.

The foregoing discussion should not be taken as a disavowal of claim scope.

SUMMARY

In at least one form, an instrument reprocessor for cleaning a medical instrument can comprise a chamber configured to receive the medical instrument, a supply of reprocessing fluid, a supply pump in fluid communication with the supply of reprocessing fluid, wherein the supply pump comprises a positive-displacement pump, and a reservoir in fluid communication with the supply pump, wherein the reservoir comprises a top and a bottom, and wherein the reservoir can comprise a reprocessing fluid height between the top and the bottom. The instrument reprocessor can further comprise a linear sensor extending between the reservoir top and the reservoir bottom, wherein the linear sensor is configured to detect the reprocessing fluid height and, in addition, a processor in signal communication with the linear sensor, wherein the processor is configured to operate the supply pump when the reprocessing fluid height is below a predetermined height, and wherein the predetermined height is between the reservoir top and the reservoir bottom. The instrument reprocessor can further comprise a dispensing pump in fluid communication with the reservoir bottom and the chamber, wherein the dispensing pump comprises a positive-displacement pump, and wherein the processor is configured to operate the dispensing pump.

In at least one form, a method of controlling the flow of reprocessing fluid through an instrument having at least a first channel and a second channel can comprise the steps of operating a pump in fluid communication with a reprocessing fluid source, flowing the reprocessing fluid through a first fluid circuit comprising a first valve and a first pressure differential sensor, wherein the first fluid circuit is in fluid communication with the pump and the first channel, and flowing the reprocessing fluid through a second fluid circuit comprising a second valve and a second pressure differential sensor, wherein the second fluid circuit is in fluid communication with the pump and the second channel. The method can further comprise the steps of detecting a first pressure differential in the reprocessing fluid flowing into the first valve utilizing the first pressure differential sensor, detecting a second pressure differential in the reprocessing fluid flowing into the second valve utilizing the second pressure differential sensor, modulating the first valve to control the first flow rate of reprocessing fluid through the first channel utilizing an output from the first pressure differential sensor, and modulating the second valve to control the second flow rate of reprocessing fluid through the second channel utilizing an output from the second pressure differential sensor.

In at least one form, an instrument reprocessor for cleaning a medical instrument including a passage can comprise a chamber configured to receive the medical instrument, a supply connector configured to be fluidly coupled with the passage, a pump configured to pressurize a reprocessing fluid and supply the reprocessing fluid to the supply connector, the pump comprising an inlet and an outlet, and a gauge pressure sensor positioned to sense the gauge pressure of the reprocessing fluid flowing from the pump outlet. The instrument reprocessor can further comprise a flow control system including a valve in fluid communication with the supply connector, wherein the valve is configured to control a flow rate of reprocessing fluid through the passage, and wherein the valve comprises an inlet and an outlet. The instrument reprocessor can further include a pressure differential sensor configured to sense a pressure drop in the reprocessing fluid on opposite sides of a fixed orifice, wherein the pressure differential sensor is positioned downstream with respect to the gauge pressure sensor and upstream with respect to the valve outlet, and a processor in signal communication with the pressure differential sensor, wherein the processor is configured to interpret the flow rate based on the pressure drop and command the valve to at least one of at least partially close and at least partially open.

In at least one form, a method of utilizing a monitoring system for maintaining a volume of reprocessing fluid within a supply reservoir for a fluid circulation system of an instrument reprocessor can comprise the steps of supplying a quantity of reprocessing fluid to the supply reservoir from a reprocessing fluid source, sensing the quantity of reprocessing fluid in the supply reservoir, and determining whether the quantity of reprocessing fluid in the supply reservoir is more than a predetermined amount. The method can further comprise the steps of operating a positive-displacement filling pump to supply reprocessing fluid to the supply reservoir if the quantity of reprocessing fluid in the supply reservoir is less than the predetermined amount, wherein the positive-displacement filling pump is configured to supply a fixed volume of reprocessing fluid per stroke, monitoring the quantity of reprocessing fluid in the supply reservoir as the positive-displacement filling pump is being operated, determining whether the quantity of reprocessing fluid in the supply reservoir has increased by a re-supply volume equal to the product of the volume displaced per stroke and the number of strokes of the positive-displacement filling pump, and broadcasting an alert if the quantity of reprocessing fluid in the supply reservoir has not increased by the re-supply volume.

In at least one form, a method of controlling the flow of reprocessing fluid through an instrument comprising a channel can comprise the steps of operating a pump in fluid communication with a reprocessing fluid source, measuring the gauge pressure of the reprocessing fluid flowing from the pump, adjusting the flow of the reprocessing fluid to adjust the gauge pressure of the reprocessing fluid, and flowing the reprocessing fluid through a fluid circuit comprising a valve and a pressure differential sensor, wherein the fluid circuit is in fluid communication with the pump and the channel. The method can further comprise the steps of detecting a pressure differential in the reprocessing fluid flowing into the valve utilizing the pressure differential sensor, and modulating the valve to control the flow rate of reprocessing fluid through the channel utilizing an output from the pressure differential sensor.

In at least one form, a method of controlling the flow of reprocessing fluid through an instrument having at least a first channel and a second channel, wherein the first channel is defined by a first value of a parameter and the second channel is defined by a second value of the parameter, can comprise the steps of initializing a pump in fluid communication with a reprocessing fluid source to begin an operating cycle, supplying the reprocessing fluid to a first fluid circuit comprising a first valve, wherein the first fluid circuit is in fluid communication with the pump and the first channel, and supplying the reprocessing fluid to a second fluid circuit comprising a second valve, wherein the second fluid circuit is in fluid communication with the pump and the second channel. The method can further comprise the step of modulating the first valve to limit the flow of reprocessing fluid through the first channel, wherein the flow of reprocessing fluid is limited by an amount based on the difference between the first value of the parameter and the second value of the parameter, whereby the reprocessing fluid flows through the first channel and the second channel when the pump is initialized.

The foregoing discussion should not be taken as a disavowal of claim scope.

DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, in some circumstances, the devices disclosed herein may be used in many orientations and positions, and these terms are not intended to be limiting and/or absolute.

Figure 1:
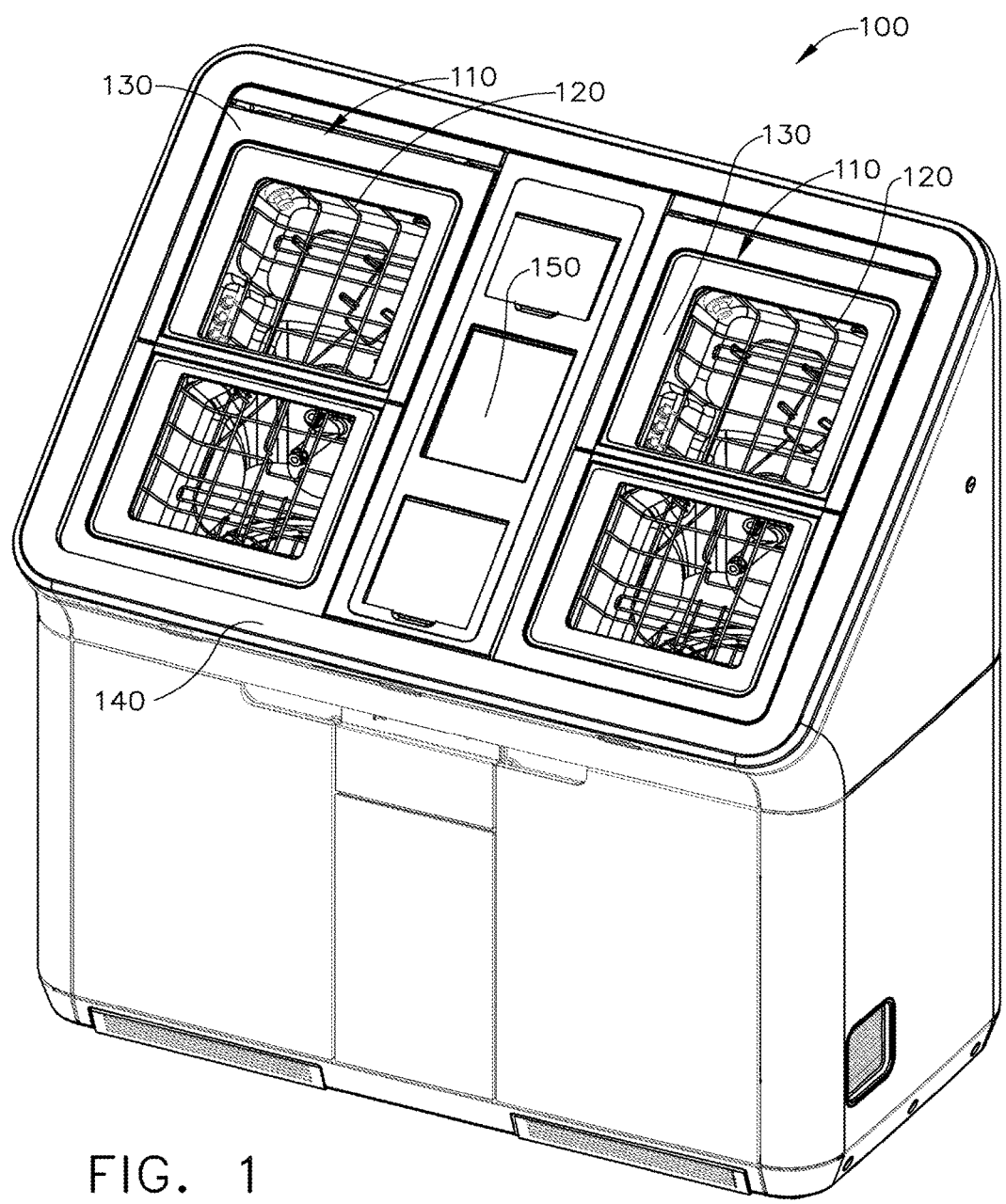
FIG. 1 is a perspective view of an endoscope reprocessor in accordance with at least one embodiment comprising two basins.
Figure 17:
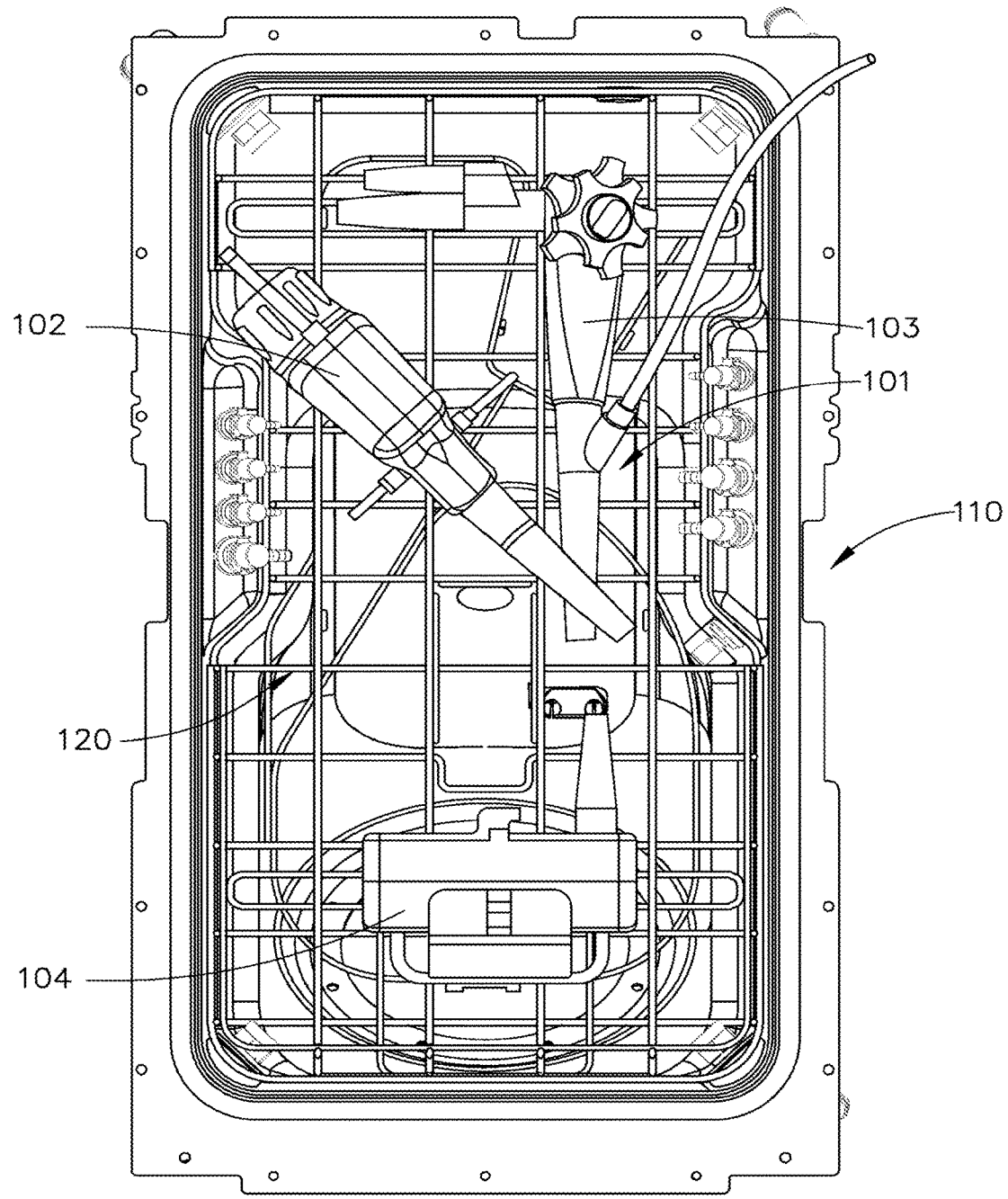
FIG. 17 illustrates an endoscope positioned within an endoscope carrier in the basin of FIG. 2.

As described above, referring to FIG. 1, a medical instrument reprocessor, such as endoscope reprocessor 100, for example, can be configured to clean one or more endoscopes. In certain embodiments, the endoscope reprocessor can be configured to disinfect and/or sterilize an endoscope. In various embodiments, the endoscope reprocessor can comprise at least one basin 110, wherein each basin 110 can be configured to receive an endoscope therein. Although the endoscope reprocessor 100 comprises two basins, for example, various alternative embodiments are envisioned which comprise any suitable number of basins 110. In various embodiments, the reprocessor 100 can further include one or more endoscope carriers 120 configured to support an endoscope therein which can be placed in each basin 110. In use, a clinician can place the endoscope into the endoscope carrier 120 and then position the endoscope carrier 120 within the basin 110. Alternatively, the clinician can position the carrier 120 in the basin 110 and then position the endoscope in the carrier 120. In either event, once the endoscope has been suitably positioned within the basin 110, a folding door 130 can be closed, secured and/or sealed to the reprocessor frame 140 in order to enclose the endoscope within the basin 110. Thereafter, the clinician can operate the endoscope reprocessor 100 by interfacing with a control panel 150, for example. Exemplary embodiments of the basin 110, the carrier 120, and the folding door 130 are described in a contemporaneously-filed, co-owned U.S. Patent Application entitled INSTRUMENT REPROCESSORS, SYSTEMS, AND METHODS, U.S. patent application Ser. No. 13/278,837, the entire disclosure of which is incorporated by reference herein. Referring now to FIG. 17, an endoscope 101 is illustrated as being positioned within a carrier 120 which is positioned in a basin 110. In various embodiments, the endoscope 101 can comprise various portions 102, 103, and/or 104 which can be supported within the carrier 120.

Figure 2:
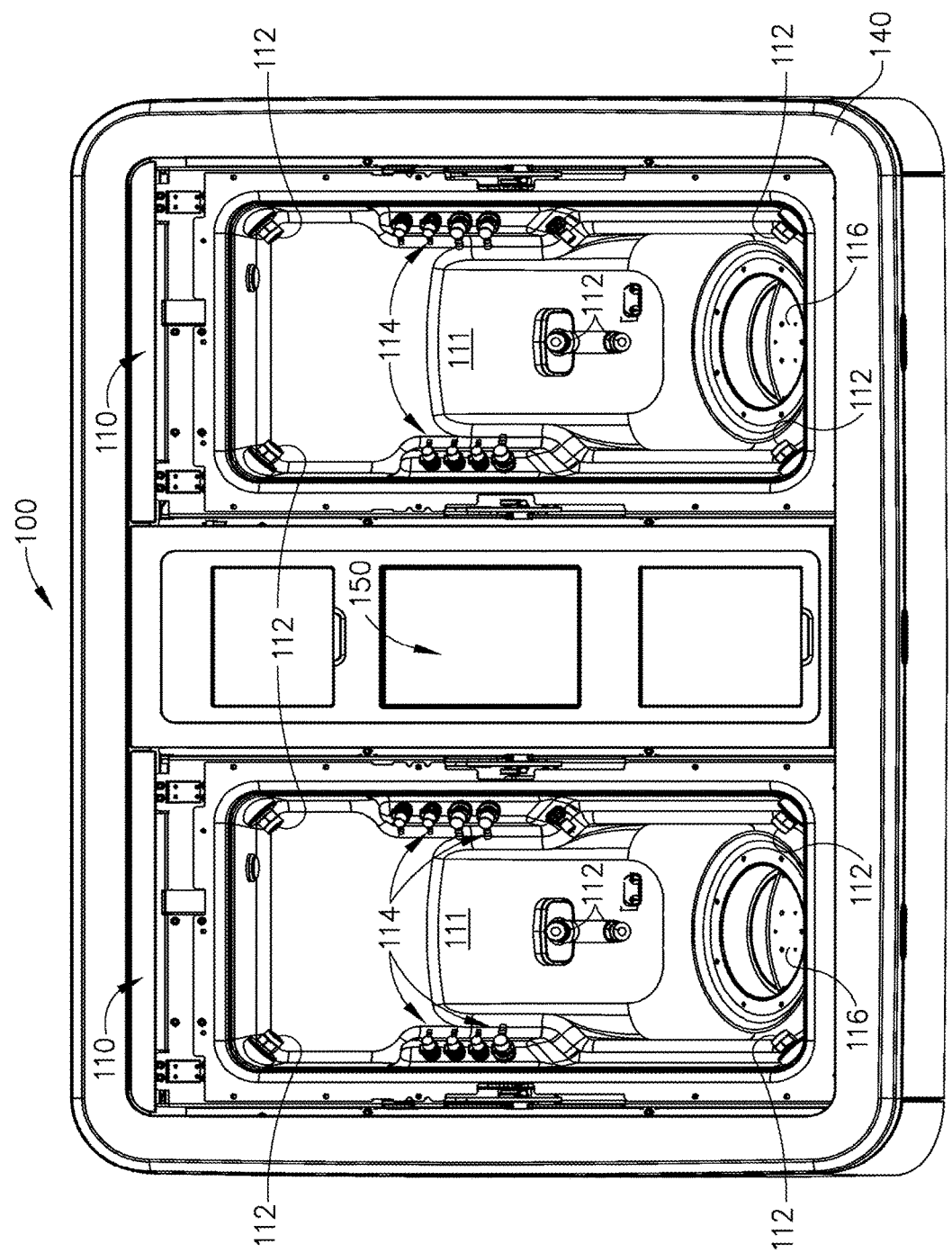
FIG. 2 is a perspective view of the basins of the endoscope reprocessor of FIG. 1.

In various embodiments, further to the above, the endoscope reprocessor 100 can include a circulation system which can circulate one or more reprocessing fluids such as detergent, sterilant, disinfectant, water, alcohol, and/or any other suitable fluid, for example, through the endoscope and/or spray the fluid onto the endoscope. The circulation system can comprise a fluid supply and a circulation pump, wherein the circulation pump can be fluidly connected to the fluid supply such that the fluid can be drawn from the fluid supply into the circulation system. In certain embodiments, the circulation system can include a mixing chamber in which the fluid can be mixed with another fluid, such as water, for example, wherein the mixing chamber can be in fluid communication with the circulation pump. In either event, referring now to FIG. 2, each basin 110 can comprise one or more spray nozzles 112 which can be in fluid communication with the circulation pump such that the fluid pressurized by the circulation pump can be ejected from the circulation system through the nozzles 112 and onto the endoscope. In at least one such embodiment, each basin 110 can include a plurality of nozzles 112 positioned around the perimeter thereof and one or more nozzles 112 which can spray upwardly from the basin floor, or backsplash, 111. Certain exemplary embodiments are described in greater detail in a contemporaneously-filed, co-owned U.S. Patent Application entitled INSTRUMENT REPROCESSORS, SYSTEMS, AND METHODS, U.S. patent application Ser. No. 13/278,837, the entire disclosure of which is incorporated by reference herein.

In various embodiments, further to the above, each basin 110 can be configured to guide the fluid sprayed therein downwardly toward a drain 116 positioned at the bottom thereof wherein the fluid can then re-enter the circulation system. In order to clean, disinfect, and/or sterilize internal channels within the endoscope, the endoscope reprocessor 100 can include one or more supply lines in fluid communication with the circulation system pump which can be placed in fluid communication with the internal channels of the endoscope. In various embodiments, referring again to FIG. 2, each basin 110 can include one or more ports 114 which can comprise the ends of the supply lines. In the illustrated embodiment, each basin 110 has a bank of four ports 114 positioned on opposite sides thereof, although other alternative embodiments are envisioned which can comprise any suitable number and arrangement of ports 114. In certain embodiments, the endoscope reprocessor 110 can further comprise one or more flexible conduits which can be connected and/or sealingly engaged with the ports 114 and the channels defined in the endoscope such that the pressurized fluid from the circulation system can flow through the ports 114, the flexible conduits, and then into the endoscope. Flexible conduits and the connectors used to sealingly engage the flexible conduits to the endoscope are described in U.S. patent application Ser. No. 12/998,459, entitled FLUID CONNECTOR FOR ENDOSCOPE REPROCESSING SYSTEM, which was filed on Aug. 29, 2011 and U.S. patent application Ser. No. 12/998,458, entitled QUICK DISCONNECT FLUID CONNECTOR, which was also filed on Aug. 29, 2011, the entire disclosures of which are incorporated by reference herein.

In various circumstances, further to the above, the channels defined within the endoscope can be become blocked or obstructed by debris, for example, which can inhibit the endoscope from being properly cleaned, disinfected, and/or sterilized. In some circumstances, the debris positioned within an endoscope channel can at least partially block the flow of the fluid therethrough thereby reducing the rate in which the fluid can flow through the channel. Various embodiments of an endoscope reprocessor are envisioned herein in which the flow rate of the fluid through an endoscope channel can be monitored to evaluate whether an obstruction exists in the channel. In such embodiments, the monitoring system could measure the actual flow rate of the fluid and compare it to flow rate of the fluid which would be expected given the pressure in which the fluid was pressurized to by the circulation pump. Certain monitoring systems could also evaluate whether the connectors of the flexible conduit are sealingly engaged with the endoscope channel and/or the basin ports 114, for example. In such systems, the monitoring system could detect whether the flow rate of the fluid is above an expected flow rate, for example. The entire disclosure of U.S. Pat. No. 7,879,289, entitled AUTOMATED ENDOSCOPE REPROCESSOR SELF-DISINFECTION CONNECTION, which issued on Feb. 1, 2011, is incorporated by reference herein.

Figure 3:
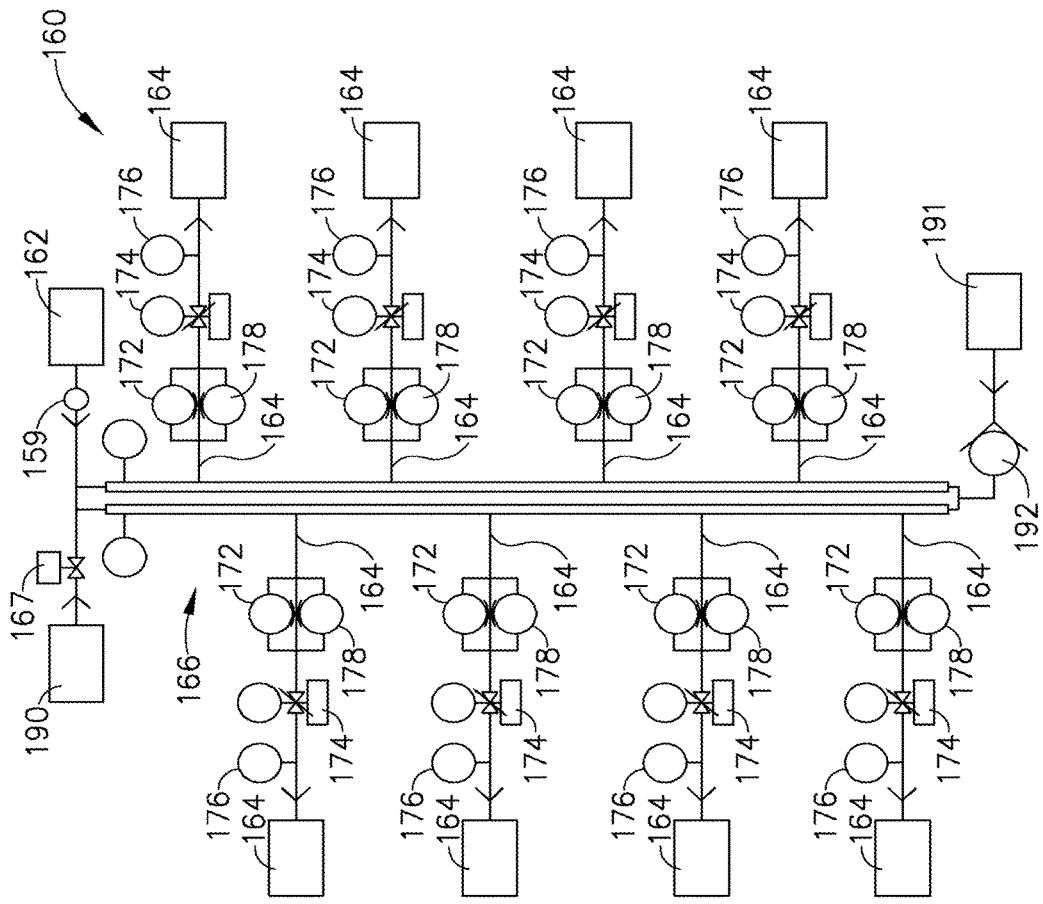
FIG. 3 is a diagram of a channel flow subsystem of the endoscope reprocessor of FIG. 1.
Figure 6:
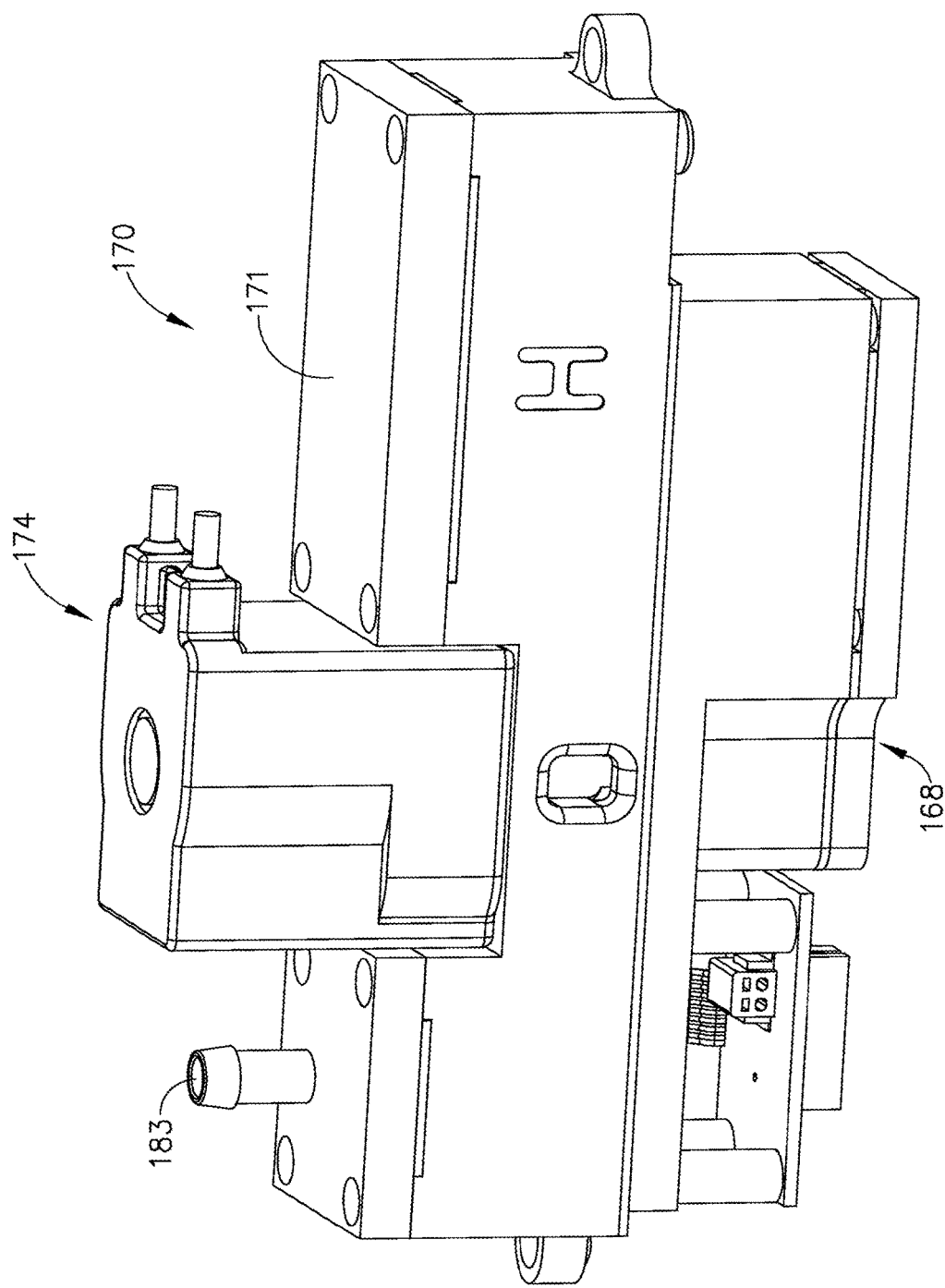
FIG. 6 is a perspective view of a flow control unit configured to control the flow of fluid through an endoscope channel supply line.
Figure 9:
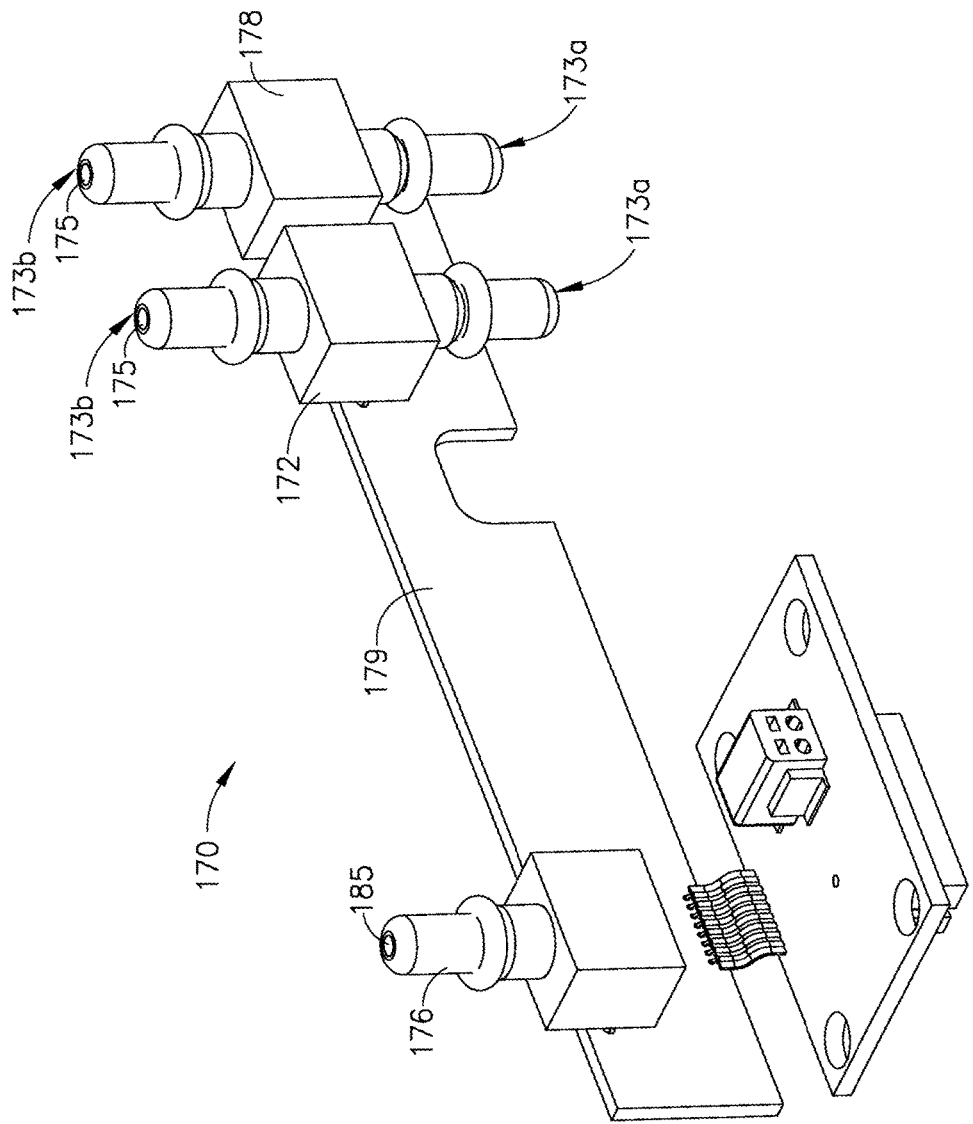
FIG. 9 is a perspective view of a subassembly of the control unit of FIG. 6 including a printed circuit board (PCB) assembly, a gauge pressure sensor, and two differential pressure sensors.
Figure 10:
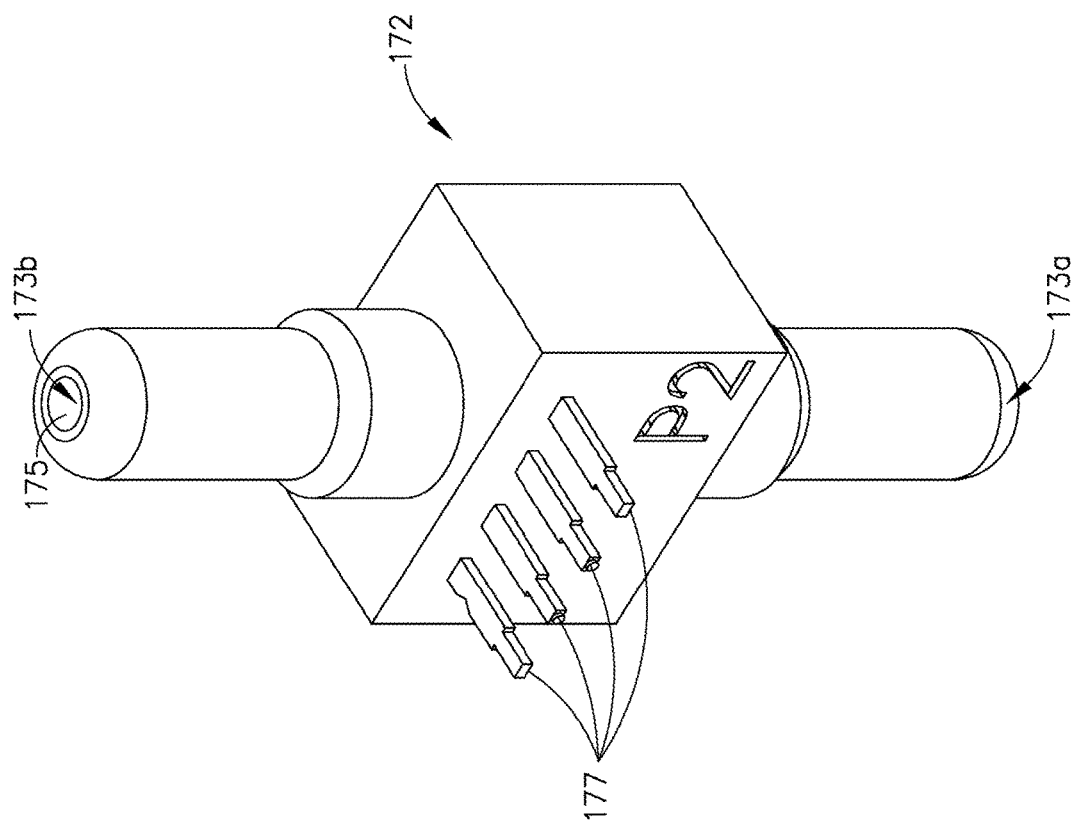
FIG. 10 is a perspective view of the differential pressure sensor of the control unit of FIG. 9.

Referring now to the diagram of FIG. 3, an endoscope reprocessor can comprise a channel flow subsystem 160 including a manifold 166 in fluid communication with the circulation system pump, indicated as pump 162, which can be configured to distribute the pressurized fluid to the channel supply lines of the endoscope reprocessor and then to the channels of the endoscope. Such channel supply lines of the endoscope reprocessor are indicated as supply lines 164 in the diagram of FIG. 3. In various embodiments, each endoscope reprocessor supply line 164 can include at least one differential pressure sensor 172, at least one proportional valve 174, and at least one gage pressure sensor 176. In certain embodiments, referring now to FIGS. 6 and 9, each reprocessor channel supply line 164 can include a control unit assembly 170 comprising a housing 171, a differential pressure sensor 172, a proportional valve 174, and a gage pressure sensor 176. In at least one such embodiment, each housing 171 can include an inlet 168 and an internal passage which can be configured to direct the flow of fluid through an inlet 173a and then an outlet 173b of the differential pressure sensor 172. Between the inlet 173a and the outlet 173b of the differential pressure sensor 172 an orifice 175 (FIG. 10) can be defined which comprises a fixed diameter. In at least one such embodiment, the diameter of the orifice 175 can be constant along the length thereof. Such an orifice could be created by a drilling process, for example. In various other embodiments, the diameter of the orifice 175 may not be constant along the length thereof. In either circumstance, such orifices can be fixed in the sense that they do not change, or at least substantially change, over time. As described in greater detail below, referring now to FIGS. 9 and 10, the differential pressure sensor 172 can further comprise a plurality of electrical contacts 177 which can place the differential pressure sensor 172 in signal communication with a printed circuit board (PCB) assembly 179 of the control unit assembly 170. The electrical contacts 177 can also be configured to supply the differential pressure sensor 172 with electrical power. Various pressure differential sensors are commercially available from Honeywell, for example.

As outlined above, the differential pressure sensor 172 can be in electrical and/or signal communication with the PCB assembly 179. More specifically, the PCB assembly 179 can include, among other things, a microprocessor and/or any suitable computer, for example, wherein the differential pressure sensor 172 can be configured to generate a voltage potential which is communicated to the microprocessor of the PCB assembly 179. In at least one such embodiment, the microprocessor of the PCB assembly 179 can be configured to interpret the voltage potential supplied by the differential pressure sensor 172 and calculate the flow rate of the fluid flowing through the differential pressure sensor 172.

In certain embodiments, further to the above, a plurality of fluid flow rate values can be stored in a look-up table defined within programmable memory on the PCB assembly 179, for example. Oftentimes, in various embodiments, the values of the expected fluid flow rates in the look-up table can be theoretically predicted while, in certain embodiments, the values can be empirically tested and then stored in the programmable memory. In either event, the fluid flow rate can be determined as a function of the gauge pressure of the fluid being discharged by the circulation pump 162 and supplied to the manifold 166. In at least one such embodiment, a gauge pressure sensor, such as gauge pressure sensor 159 (FIG. 3), for example, can be positioned downstream with respect to the outlet of the circulation pump 162 such that the gauge pressure of the fluid being supplied to each of the reprocessor channel supply lines 164 can be measured. In such embodiments, the gauge pressure sensor 159 can be placed in electrical and/or signal communication with each PCB assembly 179 of the flow control units 170 such that the gauge pressure of the fluid can be communicated to the microprocessor of each PCB assembly 179 in the form of a voltage potential. Once the gauge pressure of the fluid has been communicated to the PCB assembly 179, in various embodiments, the microprocessor can derive the fluid flow rate of the fluid from the look-up table and compare the fluid flow rate value to the target fluid flow rate. Oftentimes, the actual flow rate will not exactly match the target flow rate and, thus, a range of values for the actual flow rate between a minimum target value and a maximum target value may be acceptable.

Figure 3A:
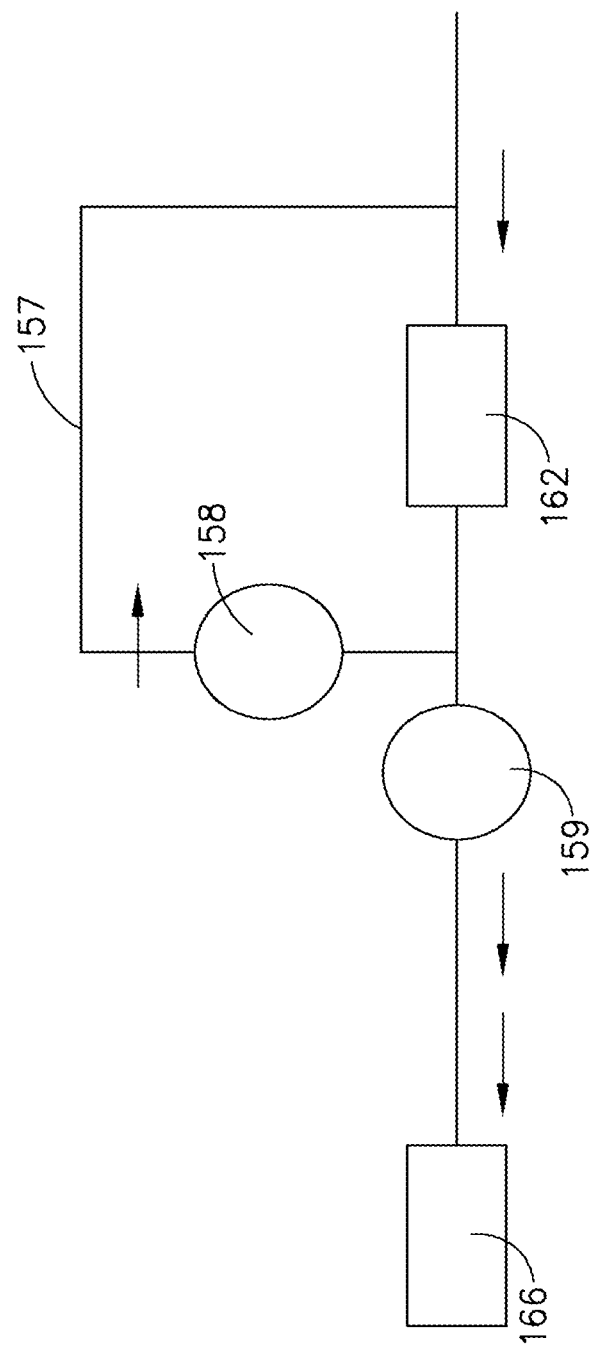
FIG. 3A is a diagram of a channel flow subsystem for controlling the pressure of the fluid flowing therethrough.
Figure 4:
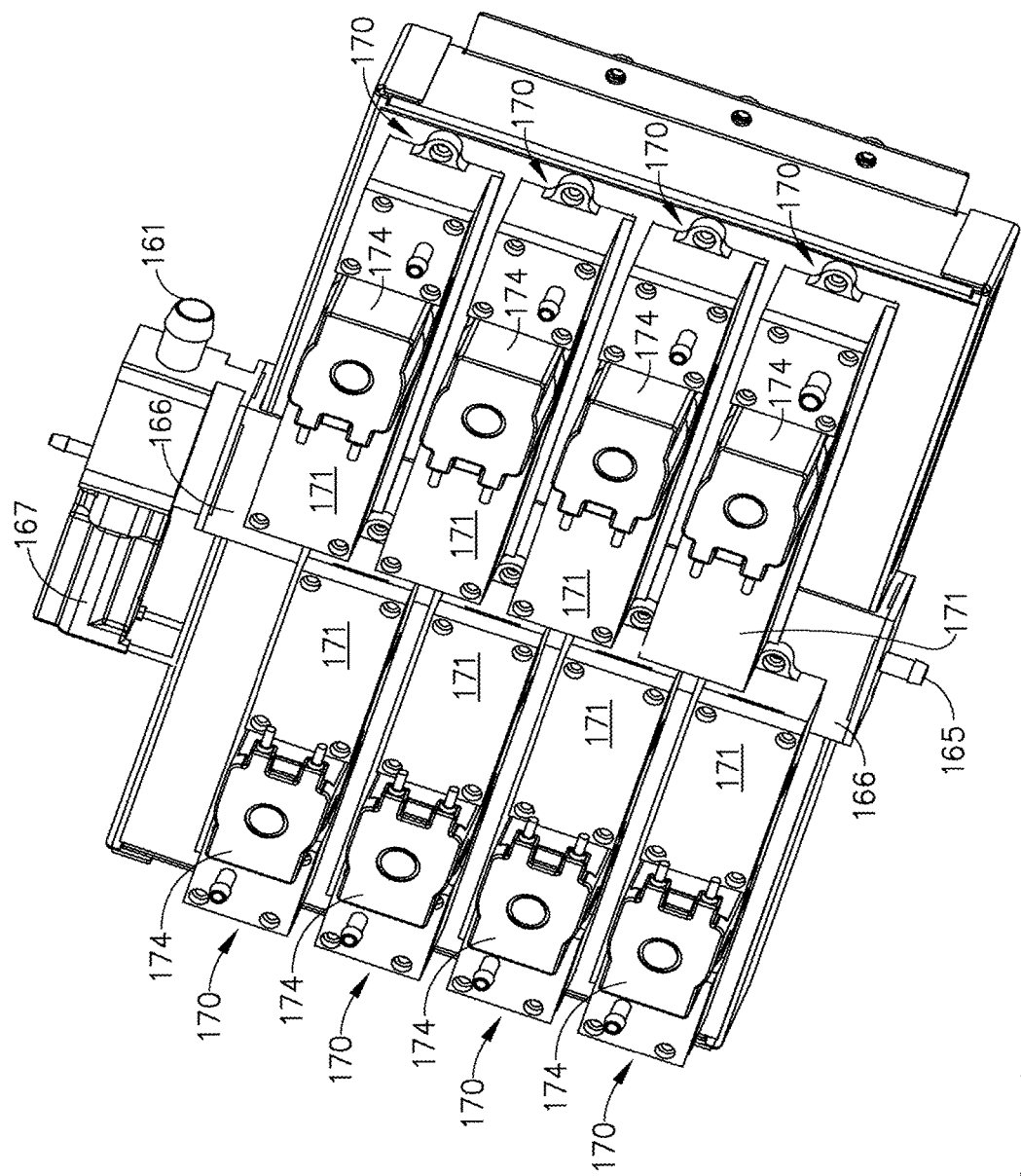
FIG. 4 is a perspective view of a manifold assembly including a plurality of flow control units.

In various embodiments, further to the above, the fluid flow rate through an reprocessor channel supply line 164 can be determined as a function of two variables, the gauge pressure reading from the gauge pressure sensor 159, as described above, and, in addition, the pressure differential reading from the differential pressure sensor 172 of a corresponding flow control unit 170. Such a system may utilize a plurality of look-up tables to derive the flow rate of the fluid. For instance, for every potential gauge pressure of the fluid that may be supplied to the manifold 166, such as 35 psi, for example, a table correlating the reading of the differential pressure sensor 172 and the expected flow rate could be stored within each PCB assembly 179. In such embodiments, a large range of gauge pressures may need to be accounted for and, thus, a large number of look-up tables may be needed. In various other embodiments, the pressure of the fluid being supplied to the reprocessor supply lines 164 may be limited to a particular pressure or a limited range of pressures. In at least one such embodiment, referring to FIG. 3A, the fluid circulation system of the instrument reprocessor 100 can include a pressure limiting valve, such as a proportional valve 158, for example, which can be in fluid communication with the outlet of the circulation pump 162 and a fluid feedback loop 157. In at least one such embodiment, the proportional valve 158 can be configured to redirect a portion the fluid being discharged by the pump 162 and return the redirected fluid to the circulation system at an inlet positioned upstream with respect to the pump 162, for example, such that the pressure of the fluid being supplied to the manifold 166 is provided at a constant, or an at least substantially constant pressure, such as 35 psig, for example. In at least one such embodiment, a PCB assembly including a microprocessor and/or any suitable computer, for example, can be utilized which is in electrical and/or signal communication with the gauge pressure sensor 159 and the proportional valve 158. In use, when the gauge pressure of the fluid is above 35 psig, for example, the PCB assembly can command the proportional valve 158 to open a certain amount, or an additional amount, to permit fluid, or more fluid, to flow through the fluid feedback loop 157. In such circumstances, such actions may lower the pressure of the fluid flowing to the manifold 166. In the event that the pressure of the fluid remains greater than 35 psig, the PCB assembly could command the proportional valve 158 to open an additional amount. Such steps could be repeated any suitable number of times to arrive at the desired pressure of the fluid. Correspondingly, when the gauge pressure of the fluid is below 35 psig, for example, the PCB assembly can command the proportional valve 158 to close a certain amount to reduce the rate of fluid flowing through the fluid feedback loop 157. In such circumstances, such actions may raise the pressure of the fluid flowing to the manifold 166. In the event that the pressure of the fluid remains lower than 35 psig, the PCB assembly could command the proportional valve 158 to close an additional amount. Such steps could be repeated any suitable number of times to arrive at the desired pressure of the fluid.

In view of the above, in various embodiments, the gauge pressure of the fluid being supplied to the flow control units 170 of the reprocessor supply lines 164 can be controlled such that it is maintained at a constant, or an at least substantially constant, pressure. Accordingly, one of the variables for calculating the flow rate of the fluid flowing through the reprocessor supply lines 164 can be held constant, or at least substantially constant. Thus, as a result, the flow rate of the fluid through each reprocessor supply line 164 and its associated control unit 170 may be a function of only one variable, i.e., the reading from the differential pressure sensor 172. In at least one such embodiment, only one look-up table may be needed to calculate the actual, calculated flow rate and/or correlate the actual, calculated flow rate with the target flow rate to determine whether the actual, calculated flow rate is between minimum and maximum acceptable values for the fluid flow rate through a reprocessor supply line 164.

Figure 7:
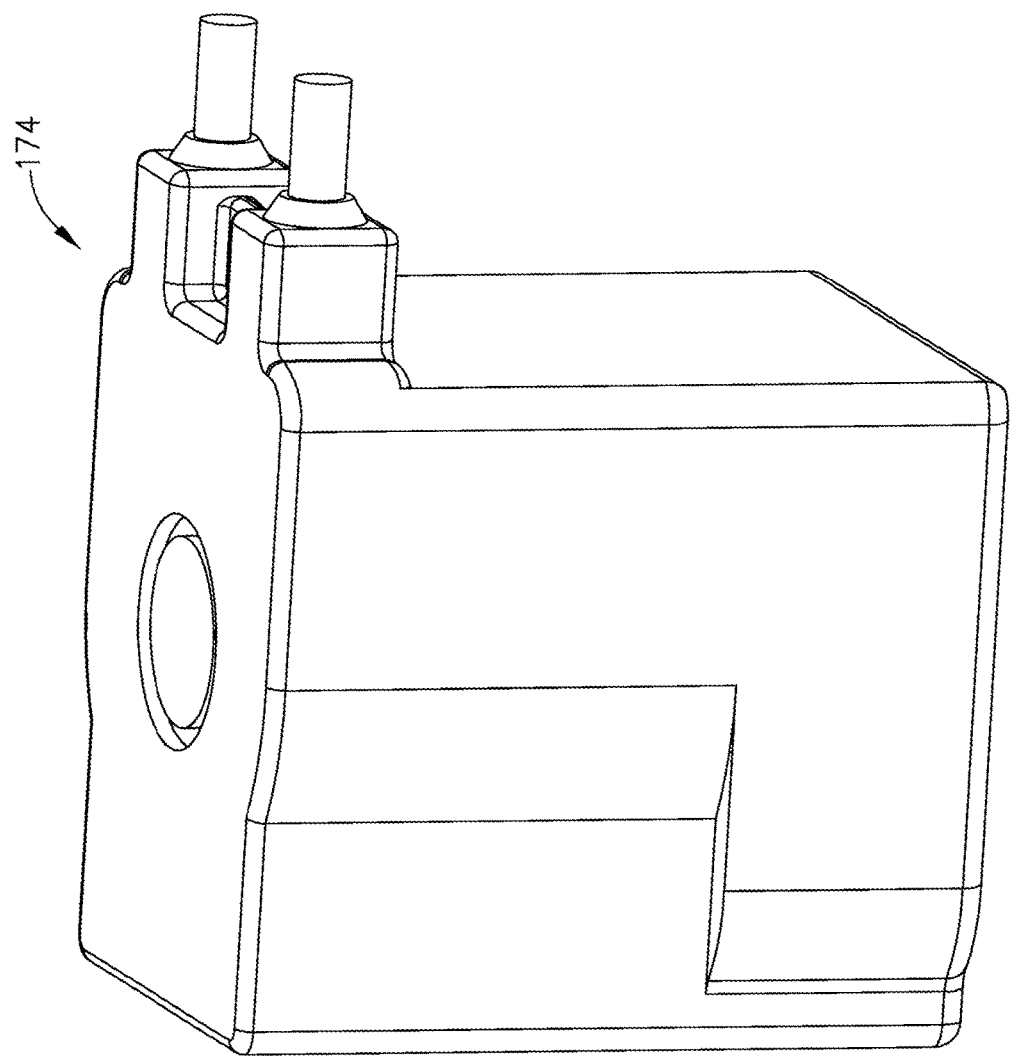
FIG. 7 is a perspective view of a proportional valve of the flow control unit of FIG. 6.
Figure 8:
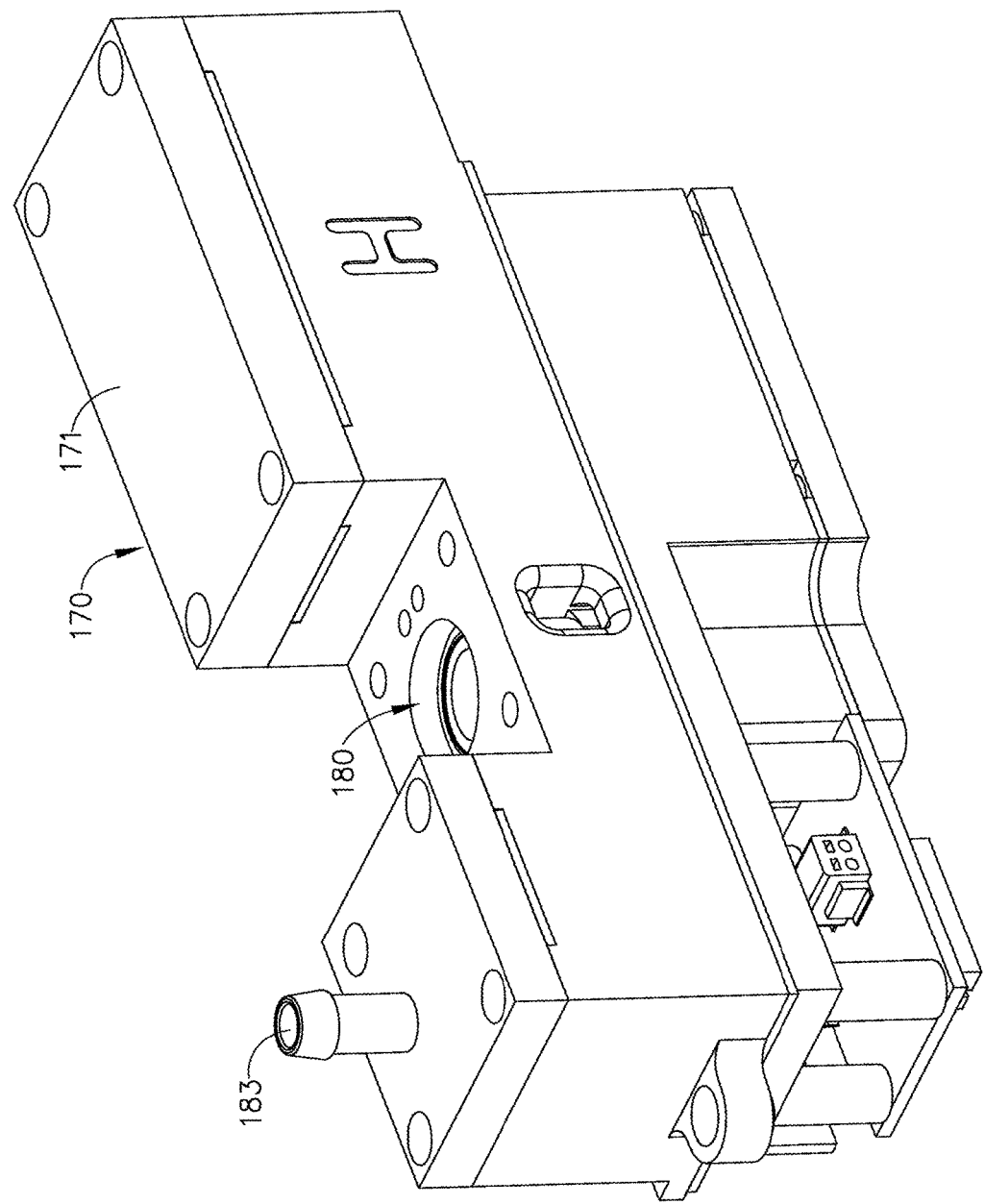
FIG. 8 is a perspective view of the flow control unit of FIG. 6 with the proportional valve of FIG. 7 removed.

In the event that the actual fluid flow rate is between minimum and maximum acceptable values for a given endoscope channel, as supplied thereto by a reprocessor supply line 164, the PCB assembly 179 of the corresponding flow control unit 170 may not adjust the proportional valve 174 and, instead, may continue to monitor the flow rate of the fluid flowing through the flow control unit 170. In the event that the actual flow rate of the fluid through the reprocessor supply line 164 is below the minimum acceptable value or above the maximum acceptable value stored in the look-up table for a given gauge pressure for a given reprocessor supply line 164, the PCB assembly 179 may open, partially open, close, and/or partially close the proportional valve 174 associated therewith. In at least one embodiment, referring to FIGS. 6-8, the proportional valve 174 can comprise an orifice or chamber 180, a valve element positioned within the chamber 180, and a solenoid which can be activated to rotate the element within the chamber 180 between an open position in which fluid can flow through the chamber, a closed position in which the element obstructs the flow of fluid therethrough, and/or any other suitable position inbetween.

In various embodiments, further to the above, the microprocessor of the PCB assembly 179 can be configured to adjust the position of the valve element within the valve chamber 180 of the proportional valve 174. In use, if the actual fluid flow rate through an reprocessor supply line 164 is higher than the target fluid flow rate, the solenoid of the proportional valve 174 can move the valve element toward its closed position to further constrict the flow of fluid therethrough. Likewise, if the actual fluid flow rate through the reprocessor supply line 164 is lower than the target fluid flow rate, the solenoid of the proportional valve 174 can move the valve element toward its open position to reduce the constriction to the fluid flowing therethrough. In various embodiments, the valve element can be rotated from an open position to a first position to constrict a valve orifice a first amount, such as approximately 25%, for example, to a second position to constrict the valve orifice a second amount, such as approximately 50%, for example, to a third position to constrict the valve orifice a third amount, such as approximately 75%, for example, and to a closed position in which the valve orifice is approximately 100% constricted, for example. In various embodiments, the valve element of the proportional valve 174 can be positionable in any suitable number of positions to provide a desired constriction to the flow of fluid through the valve 174. In any event, the position of the valve element can be controlled by a voltage potential applied to the valve solenoid by the PCB assembly 179 wherein, for example, a lower voltage potential applied to the valve solenoid can result in the valve element being oriented in a position which is closer to its fully-closed position as compared to when a higher voltage potential is applied to the valve solenoid which orients the valve element in a position which is closer to its fully-open position, for example.

In various circumstances, as a result of the above, the PCB assembly 179 can be configured to continuously monitor the flow rate of the fluid flowing through a reprocessor supply line 164 and adjust the proportional valve 174 to increase and/or reduce the rate of fluid flowing through the reprocessor supply line 164 and, correspondingly, the endoscope channel fluidly coupled thereto. In various embodiments, further to the above, the PCB assembly 179 can be configured to keep the flow rate of the fluid at and/or near a desired flow rate. In embodiments where the fluid being circulated is a sterilant or a solution including a sterilant, for example, the sterilant can sterilize the endoscope; however, the sterilant may also negatively affect or degrade the endoscope. Thus, in view of the above, the channel flow subsystem 160 can be configured to supply a sufficient minimum flow of sterilant to the endoscope in order to sterilize the endoscope yet limit the maximum flow of sterilant to the endoscope such that the sterilant does not overly degrade the endoscope. Similarly, in view of the above, the channel flow subsystem 160 can be configured to supply a sufficient minimum flow of disinfectant to the endoscope in order to disinfect the endoscope yet limit the maximum flow of disinfectant to the endoscope such that the disinfectant does not overly degrade the endoscope. In various embodiments, each endoscope channel supply line can further include a second differential pressure sensor, such as differential pressure sensor 178, for example, which can also detect the flow rate of the fluid through the reprocessor supply line 164. In at least one such embodiment, the first differential pressure sensor 172 and the second differential pressure sensor 178 of a control unit assembly 170 can be placed in parallel with one another wherein, in the event that the pressure sensors 172 and 178 supply appreciably different voltage readings to the PCB assembly 179, the PCB assembly 179 can execute a corrective action routine which could include closing the proportioning valve 174, for example, and/or issuing an alert or warning to the operator that the control unit assembly 170 may need to be serviced.

As outlined above, each proportional valve 174 can be configured to control the condition of a variable orifice. In at least one such embodiment, each proportional valve 174 can comprise a biasing element, such as a spring, for example, which can be configured to bias the valve element of the proportional valve 174, discussed above, into a normally-closed condition. The solenoid of the proportional valve 174, as also discussed above, can be actuated to move the valve element into an at least partially open position. In at least one embodiment, a series of voltage pulses can be applied to the solenoid from the corresponding PCB assembly 179 which can control the degree, or amount, in which the valve element is opened. In at least one such embodiment, the greater frequency in which the voltage pulses are applied to the solenoid, the larger the variable orifice can be thereby permitting a larger flow rate of fluid therethrough. Correspondingly, the lower frequency in which the voltage pulses are applied to the solenoid, the smaller the variable orifice can be thereby permitting a smaller flow rate of fluid therethrough. If the voltage pulses are no longer applied to the solenoid of the proportional valve 174, the biasing element can move the valve element into a closed condition once again. Other various embodiments are envisioned in which the valve element is biased into a normally-open condition and the solenoid of the proportional valve can act to bias the valve element into an at least partially closed condition. In various other embodiments, a valve for controlling the orifice can be configured to cycle a valve element between a fully open position and a fully closed position and control the rate of fluid flowing therethrough by controlling the time in which the valve element is closed as compared to the time in which the valve element is open. In at least one such embodiment, the valve element can be cycled rapidly between its open and closed conditions by a solenoid, for example.

Figure 11:
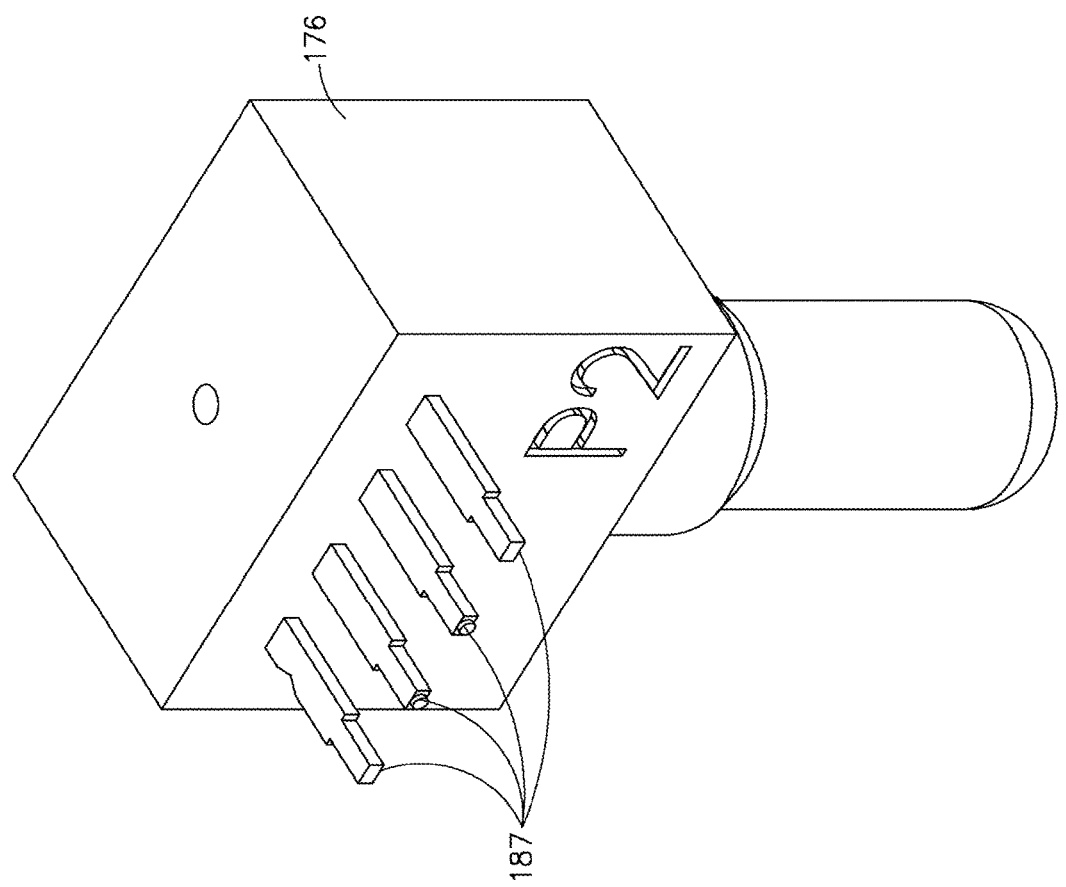
FIG. 11 is a perspective view of the gauge pressure sensor of the control unit of FIG. 9.
Figure 12:
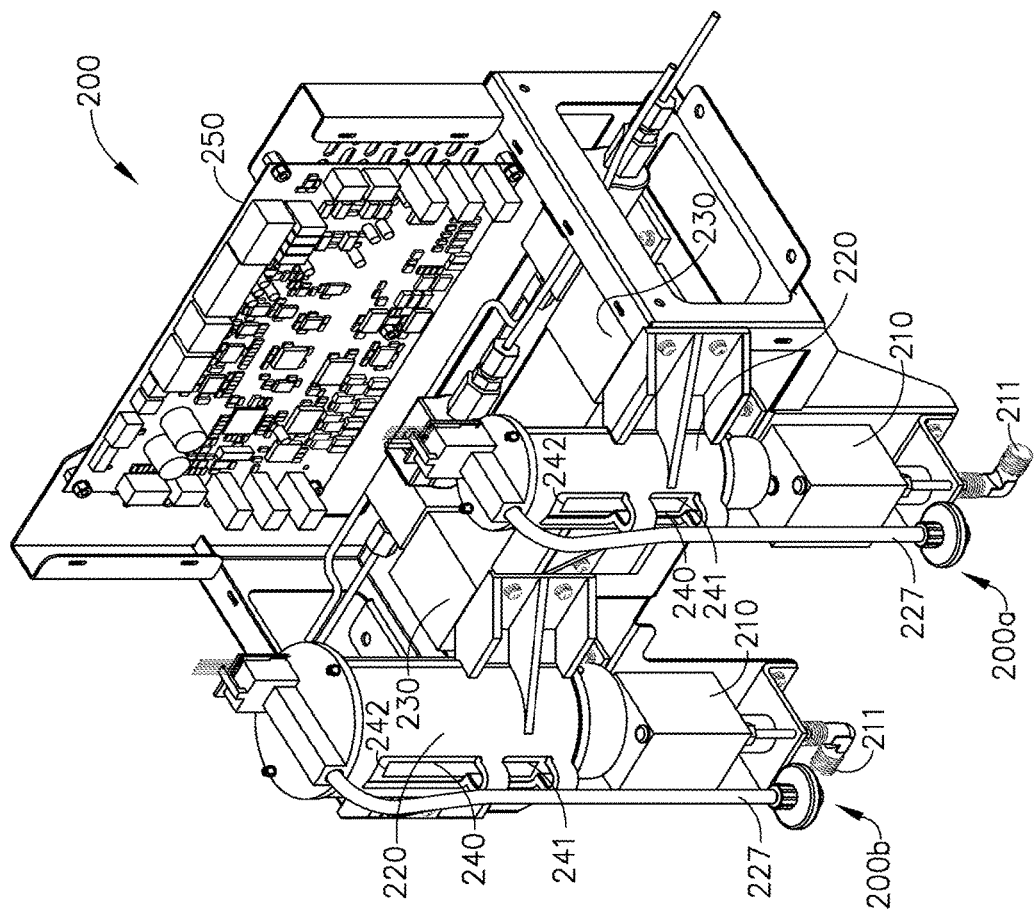
FIG. 12 is a perspective view of a fluid delivery system.
Figure 13:
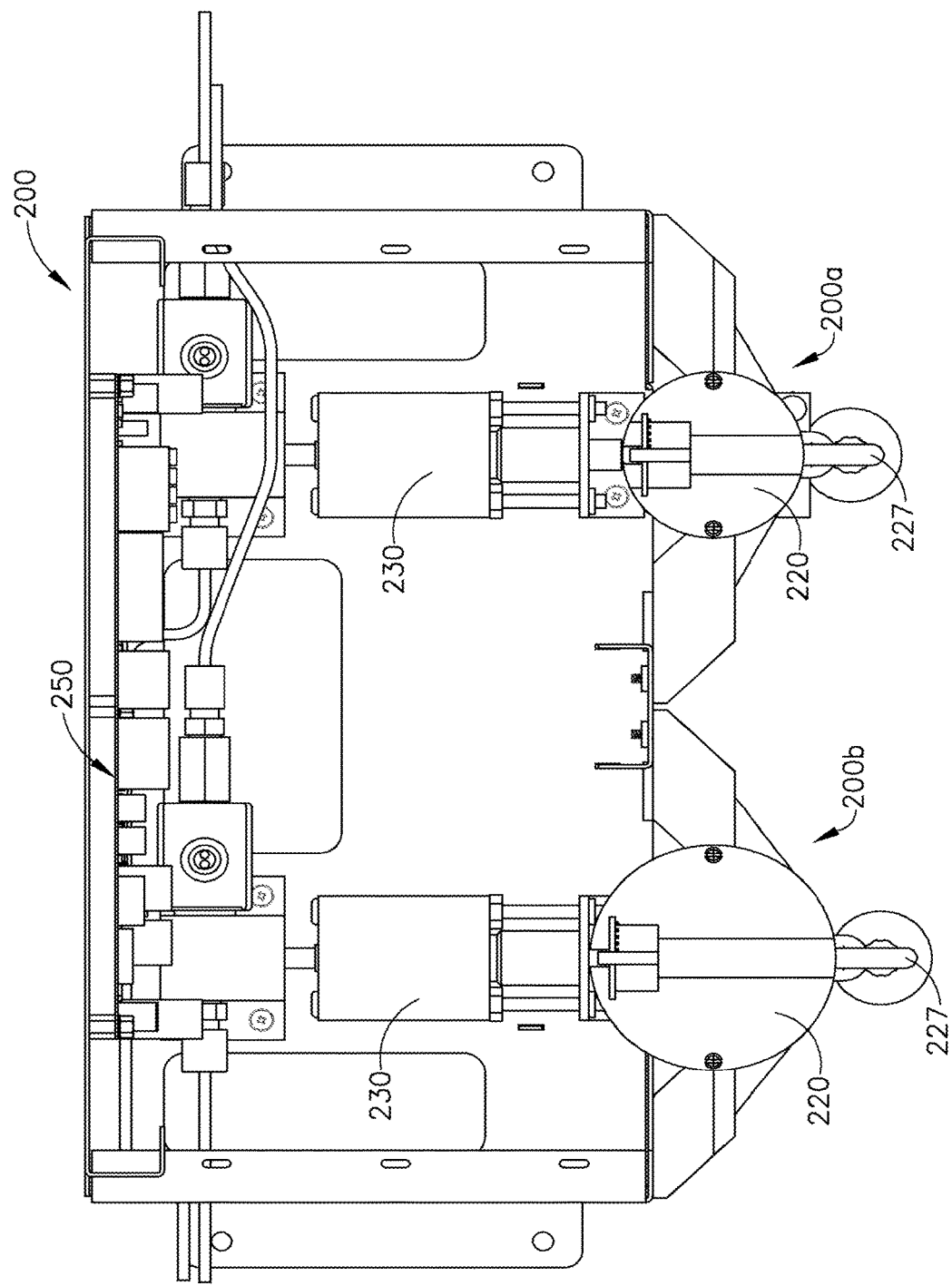
FIG. 13 is a top view of the fluid delivery system of FIG. 12.
Figure 14:
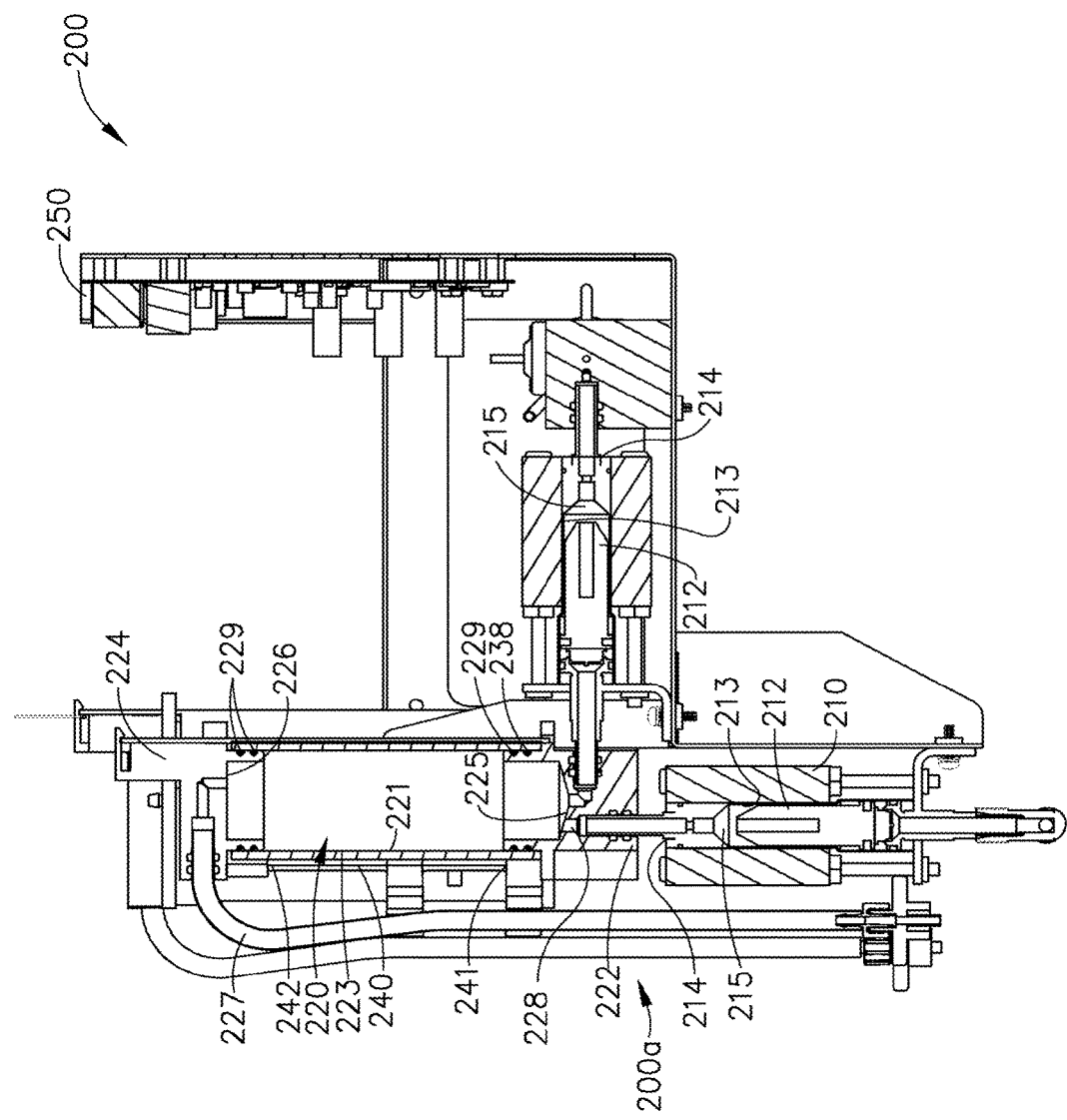
FIG. 14 is a cross-sectional elevational view of the fluid delivery system of FIG. 12.
Figure 15:
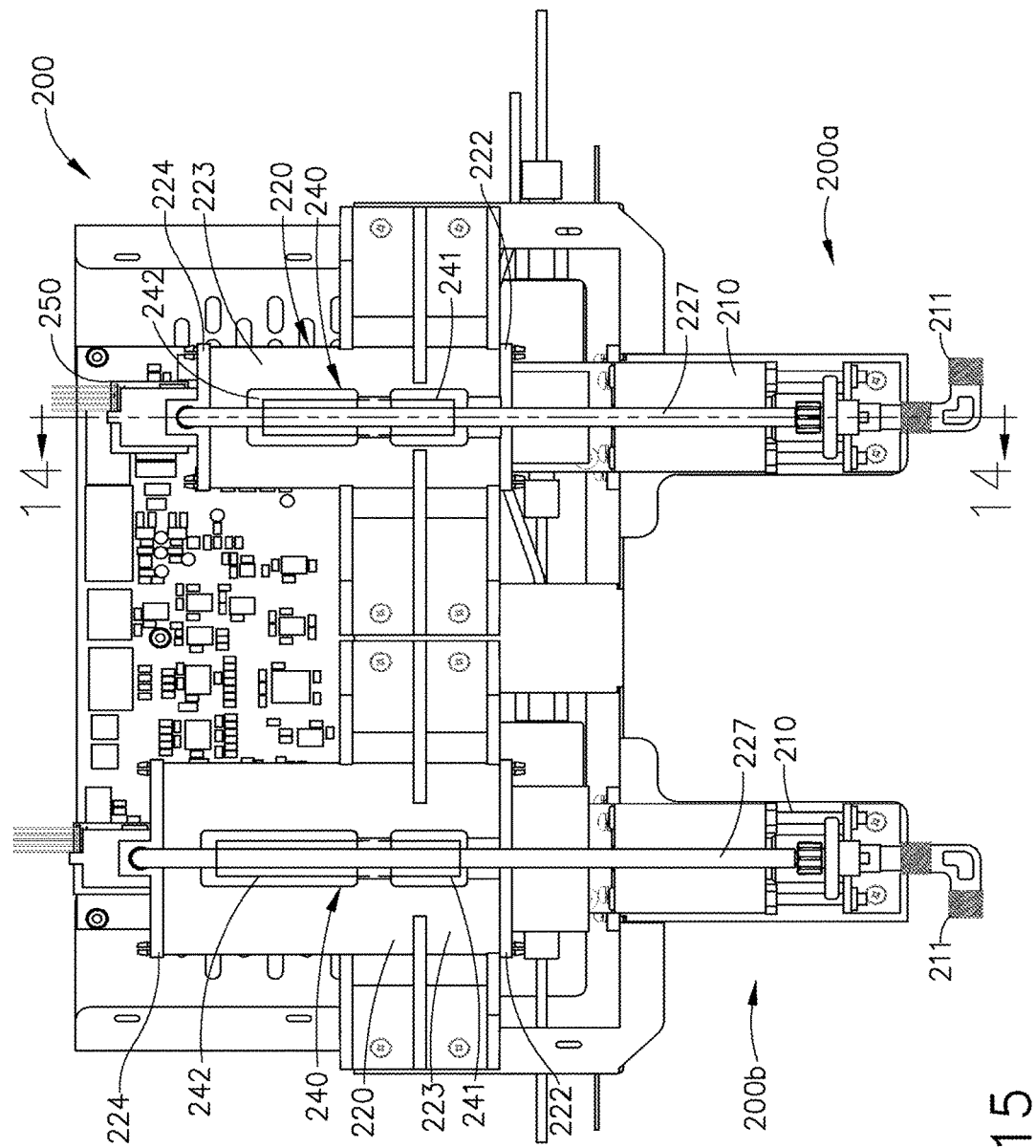
FIG. 15 is an elevational view of the fluid delivery system of FIG. 12.

Further to the above, each reprocessor supply line 164 can include a control unit assembly 170 wherein the control unit assemblies 170 can be configured to control the flow of fluid through the reprocessor supply lines 164 independently of another. In various embodiments, the control unit assemblies 170 may not be in electrical and/or signal communication with each other. In such embodiments, each control unit assembly 170 is configured to monitor and adjust the flow rate of the fluid flowing through a reprocessor supply line 164 without communicating with the other control unit assemblies 170. In various other embodiments, however, the control unit assemblies 170 can be in electrical and/or signal communication with each other such that certain parameters of the fluid within the reprocessor supply lines 164 could be compared to one another, for example. In either event, the PCB assembly 179 of a control unit 170 can be programmed to fully open the proportional valve 174 thereof in the event that the gauge pressure exiting the control unit 170 exceeds a predetermined maximum pressure, such as approximately 21.75 psig, for example. In various embodiments, the gauge pressure sensor 176 of a control unit assembly 170, mentioned above, can be configured to, one, detect the gauge pressure of the fluid exiting the proportional valve 174 of a reprocessor supply line 164 and, two, communicate a voltage potential to its respective PCB assembly 179 which can interpret the voltage potential into a gauge pressure. As compared to the differential pressure sensors 172 and 178 which can detect a pressure drop in the fluid between two points in a fluid supply line, the gauge pressure sensors 176 can detect the actual pressure of the fluid, or gauge pressure. In various embodiments, referring to FIGS. 9 and 11, a gauge pressure sensor 176 can comprise a passage 185 which can be configured to direct the flow of fluid past a sensing element and to an outlet 183 of the flow control unit 170. Similar to the above, each gauge pressure sensor 176 can comprise a plurality of electrical contacts 187 which can place the gauge pressure sensor 176 in electrical and/or signal communication with its corresponding PCB assembly 179.

Figure 5:
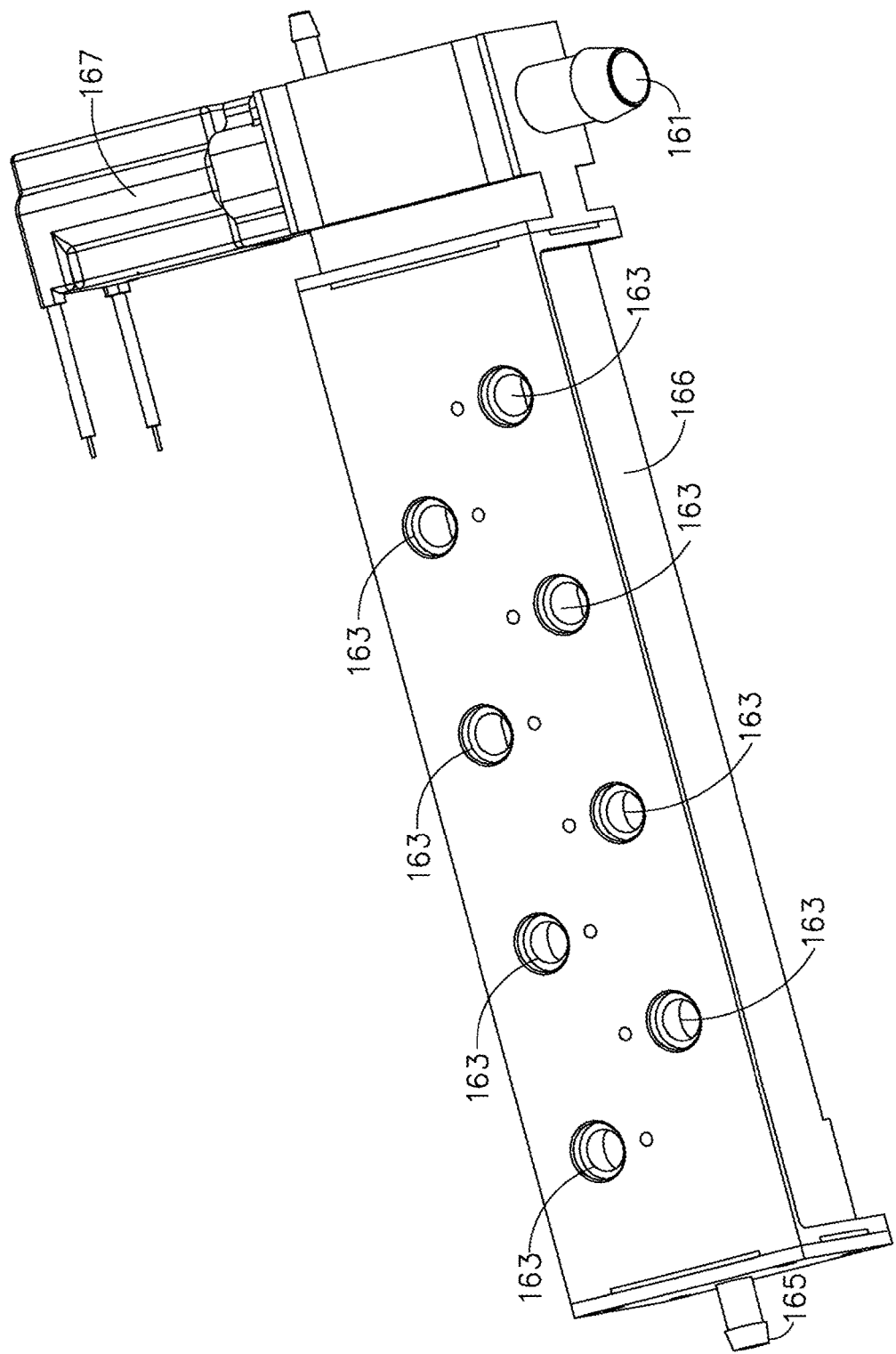
FIG. 5 is a perspective view of the manifold of the manifold assembly of FIG. 4.

Further to the above, the manifold 166 of the fluid circulation system 160 can be configured to distribute the fluid flowing therethrough to eight endoscope reprocessor supply lines 164 and the endoscope channels associated therewith. Referring now to FIG. 5, the manifold 166 can include an inlet 161, eight outlets 163, and a second inlet 165 positioned on an opposite end of the manifold 166. In various embodiments, the manifold 166 can be configured to receive and distribute several different fluids throughout the operation of the endoscope reprocessor 100. Referring to FIG. 3 once again, the inlet 161 of the manifold 166 can be configured to receive a flow of solution comprising water and detergent, among other things, from pump 162. In various embodiments, one or more valves can be operated to place the pump 162 in fluid communication with a source of water such that the pump 162 can pump water into the supply lines 164. In certain embodiments, one or more valves can be operated to place the pump 162 in fluid communication with a source of sterilant, or sterilant solution, such that the pump 162 can pump the sterilant into the supply lines 164. In at least one embodiment, referring again to FIG. 5, the endoscope reprocessor 100 can comprise one or more valves, such as valve 167, for example, which can be operated to permit a flow of pressurized air from a pressurized air source 190, for example, into the manifold 166. In at least one such embodiment, the pressurized air can force any remaining water, detergent, and/or sterilant out of the endoscope channels. In certain embodiments, the endoscope reprocessor 100 can further comprise a supply of alcohol 191 and a pump which can be configured to draw alcohol from the alcohol supply 191 and introduce the alcohol into the manifold 166 through the second inlet 165, for example. In at least one such embodiment, a check valve 192 can be positioned intermediate such a pump and the second inlet 165 such that other fluids from the manifold 166 cannot flow into the alcohol supply 191.

In view of the above, an instrument reprocessor can be configured to supply one or more pressurized fluids to the channels of an instrument, such as an endoscope, for example. In various embodiments, the flow rates of the fluids being supplied to the endoscope channels can be monitored. In the event that the flow rate of the fluid being supplied to an endoscope channel is below a target flow rate or a minimum acceptable flow rate, the instrument reprocessor can increase the flow rate of the fluid flowing therethrough. In the event that the flow rate of the fluid being supplied to an endoscope channel is above a target flow rate or a maximum acceptable flow rate, the instrument reprocessor can decrease the flow rate flow of the fluid flowing therethrough. In certain embodiments, the instrument reprocessor can include a plurality of supply lines supplying the endoscope channels with fluid wherein each supply line can include a variable valve orifice which can be modulated to adjust the flow rate of the fluid passing therethrough. In various embodiments, the variable valve orifice of each supply line can be part of a closed loop arrangement which includes a fixed orifice pressure differential sensor configured to sense the flow rate of the fluid. In various embodiments, the pressure differential sensor can be positioned upstream with respect to the variable valve orifice and downstream with respect to a circulation pump. In at least one embodiment, the instrument reprocessor can further include a gauge pressure sensor for sensing the gauge pressure of the fluid exiting the circulation pump and a pressure control system which can be configured to modulate the pressure of the fluid relative to a targeted pressure. In at least one such embodiment, the differential pressure sensor can be positioned downstream with respect to the gauge pressure sensor and the pressure control system.

Figure 16:
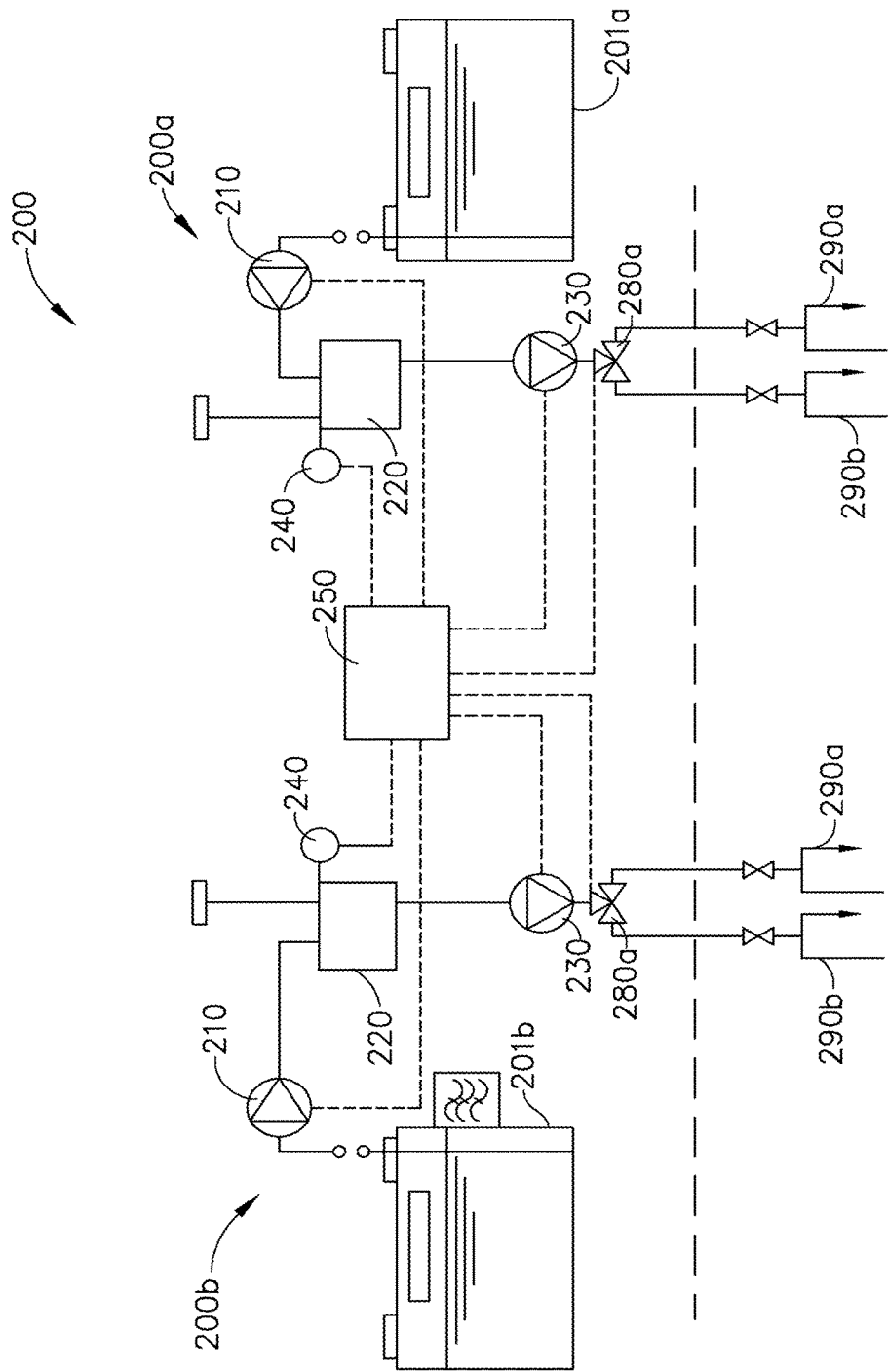
FIG. 16 is a schematic of the fluid delivery system of FIG. 12.

As described above, the fluid circulation system of the endoscope reprocessor 100 can be configured to circulate a fluid through an endoscope and/or spray the fluid onto the outside surface of the endoscope. In various embodiments, referring now to FIG. 8, the endoscope reprocessor 100 can comprise a fluid dispensing system 200 which can be configured to dispense one or more fluids to the fluid circulation system. In various embodiments, referring now to FIGS. 12-16, the fluid dispensing system 200 can comprise two or more separate fluid dispensing subsystems, such as fluid dispensing subsystems 200a and 200b, for example, which can each be configured to dispense a different fluid, for example, to the fluid circulation system. In various embodiments, referring now to FIG. 16, the endoscope reprocessor 100 can include a storage area which can be configured to house one or more containers of a fluid, such as sterilant container 201a and/or detergent container 201b, for example, therein wherein the endoscope reprocessor 100 can further include one or more fluid connectors which can each be sealingly engaged with one of the fluid containers. In certain embodiments, the endoscope reprocessor 100 can further comprise a RFID reader and/or a bar code reader which can be configured to read a RFID tag and/or a bar code on the fluid container to ensure that, one, the correct fluid is being used and, two, that the fluid is being used by a certain expiration date, for example. In any event, once the fluid connector has been coupled to the fluid container, the fluid dispensing system 200 can be configured to draw the fluid from the fluid container and dispense it into the circulation system, as described in greater detail further below.

In various embodiments, further to the above, the fluid subsystem 200a can include a supply pump 210, a reservoir 220, and a dispensing pump 230. In certain embodiments, the supply pump 210 can include an inlet 211 in fluid communication with the fluid container and/or any other suitable fluid source. In at least one embodiment, the supply pump 210 can comprise a positive displacement pump which, in at least one such embodiment, can comprise a piston configured to displace a fixed amount of volume, or fluid, per stroke of the piston. More specifically, referring primarily to FIG. 14, the supply pump 210 can comprise a piston 212 which can be configured to move, or reciprocate, within a cylinder 213 between a first, or bottom dead center (BDC) position, and a second, or top dead center (TDC) position, in order to draw fluid into the cylinder 213 and push the fluid through cylinder outlet 214. In certain embodiments, the supply pump 210 can further comprise a valve lifter 215 which can be contacted by the piston 212 to open a valve element and allow the fluid to exit through the pump outlet 214 when the piston 212 reaches its TDC position. When the piston 212 is returned to its BDC position, a valve spring positioned behind the valve lifter 215, for example, can be configured to return the valve element and the valve lifter 215 to a seated position in which the outlet 214 is sealingly closed until the valve element and the valve lifter 215 are lifted once again by the piston 212 during the next stroke thereof. As described in greater detail below, the outlet 214 of the supply pump 210 can be in fluid communication with the reservoir 220 such that the fluid pressurized by the supply pump 210 can be discharged into an internal cavity 221 defined in the reservoir 220.

In various embodiments, the reservoir 220 can include a bottom portion 222, a housing 223, and a top portion 224, wherein, in at least one embodiment, the outlet 214 of the supply pump 210 can be in fluid communication with the internal cavity 221 of the reservoir 220 through a port 228 the bottom portion 222, for example. In other various embodiments, the supply pump 210 can be in fluid communication with the reservoir cavity 211 through a port in the housing 223 and/or the top portion 224, for example. In any event, the bottom portion 222 and the top portion 224 can be sealingly engaged with the housing 223 wherein, in at least one embodiment, the bottom portion 222 and the top portion 224 can be configured to engage the housing 223 in a snap-fit and/or press-fit arrangement, for example. In various embodiments, the bottom portion 222 and the top portion 224 can be comprised of a plastic material which may not degraded by the fluid contained within the reservoir 220, for example. In certain embodiments, the reservoir 220 can further include a seal, such as an O-ring 229, for example, which can be positioned intermediate the bottom portion 222 and the housing 223 and a seal, such as an O-ring 229, for example, positioned intermediate the housing 223 and the top portion 224 which can prevent fluids from leaking out of the reservoir 220. In various embodiments, the housing 223 can be comprised of any suitable material, such as glass, for example. In at least one embodiment, the housing 223 can be comprised of borosilicate, for example, which may not be degraded by the fluid contained within the reservoir 220.

As discussed above, the supply pump 210 can be configured to supply a fixed quantity of fluid to the internal reservoir cavity 221 for each stroke of the supply pump piston 212. In use, the supply pump 210 can be operated a suitable number of times, or cycles, in order to fill the internal cavity 221 and/or fill the internal cavity 221 above a predetermined level, or height, within the internal cavity 221. In certain embodiments, the reservoir 220 can include an overflow line 227 which can be configured to vent fluid back to the fluid source, for example, in the event that the reservoir 220 is overfilled. In various embodiments, referring again to FIG. 14, the internal cavity 221 can have a bottom 225, a top 226, and a height defined between the bottom 225 and the top 226. In at least one such embodiment, the internal cavity 221 can be cylindrical and can have a constant circumference along the height thereof while, in other embodiments, the internal cavity 221 can have any suitable configuration. In various embodiments, as a result of the above, each cycle of the supply pump 210 can raise the height of the fluid within the internal reservoir cavity 221 a certain, or fixed, amount. In at least one embodiment, the amount of fluid in the reservoir 220 can be maintained by operating the supply pump 210 the same number of strokes that the dispensing pump 230 has been operated, for example. In certain embodiments, the reservoir 210 can comprise a sensor, such as level sensor 240, for example, which can be configured to detect the height of the fluid within the reservoir cavity 221 and/or changes in the height of the fluid within the reservoir cavity 221, as described in greater detail below.

In various embodiments, further to the above, the level sensor 240 can comprise an analog sensor and can be mounted to the reservoir housing 223. In at least one embodiment, the housing 223 can be comprised of glass and the level sensor 240 can be attached to the glass using at least one adhesive, for example. In at least one such embodiment, the level sensor can comprise a capacitive sensor, such as a linear capacitive sensor, for example, which can have a first end 241 positioned at or adjacent to the bottom 225 of the reservoir cavity 221 and a second end 242 positioned at or adjacent to the top 226 of the reservoir cavity 221. In such embodiments, the level sensor 240 can be configured to generate a first, or low, voltage when the internal cavity 211 is empty, or at least substantially empty, and a second, or high, voltage when the internal cavity 211 is full, or at least substantially full. In addition, the level sensor 240 can be configured to generate a range of voltages between the low voltage and the high voltage, depending on the level of the fluid within the reservoir cavity 211. More particularly, in various embodiments, the voltage generated by the level sensor 240 can be a function of the fluid height within the reservoir cavity 221 and, thus, the voltage can increase as the fluid height increases. In at least one such embodiment, the voltage can be linearly proportional to the fluid height, for example, wherein, in at least one embodiment, the low voltage can be approximately zero volts and the high voltage can be approximately five volts, for example.

In various embodiments, the fluid dispensing subsystem 200a can further comprise a dispensing pump 230 which can be in fluid communication with the internal cavity 211 of the reservoir 210 and can be configured to draw the fluid from the reservoir cavity 211 and dispense the fluid into the fluid circulation system, and/or a mixing chamber within the fluid circulation system, of the endoscope reprocessor 100. In at least one embodiment, the inlet to the dispensing pump 230 can be in fluid communication with the bottom 225 of the internal chamber 221 through a port 238 in the bottom portion 222 of the reservoir 220. In certain embodiments, the dispensing pump 230 can comprise a positive displacement pump which can be configured to displace a fixed volume of fluid per stroke. A positive displacement pump is described in detail in connection with the supply pump 210 and such discussion is not repeated herein for the sake of brevity. In some embodiments, the supply pump 210 and the dispensing pump 230 can be identical, or at least nearly identical. In at least one embodiment, the dispensing pump 230 can be configured to displace the same, or at least substantially the same, amount of volume, or fluid, per stroke as the supply pump 210.

In use, the supply pump 210 can be operated to fill the internal chamber 221 of the reservoir 220 until the fluid level has met or exceeded a predetermined height within the chamber 221. In various embodiments, the fluid dispensing subsystem 200a can comprise a computer, or microprocessor, such as PCB assembly 250, for example, which can in be in electrical and/or signal communication with the supply pump 210, the dispensing pump 230, and/or the level sensor 240. In at least one such embodiment, the PCB assembly 250 can be configured to detect the voltage potential generated by the level sensor 240 and calculate the fluid height within the reservoir 220 as a function of the voltage potential. In the event that the PCB assembly 250 calculates that the fluid level within the reservoir 220 is below the predetermined height, the PCB assembly 250 can operate the fluid supply pump 210 until the fluid level has met or exceeded the predetermined height. In at least one embodiment, the PCB assembly 250 may not operate the dispensing pump 230 when the fluid level in the reservoir 220 is below the predetermined height. In the event that the PCB assembly 250 calculates that the fluid level in the reservoir 220 is at or above the predetermined height, the PCB assembly 250 can operate the dispensing pump 230 to supply the fluid circulation system with the fluid, when needed. In certain embodiments, the PCB assembly 250 can be configured to operate the supply pump 210 in advance of operating the dispensing pump 230 such that a sufficient supply of fluid exists in the reservoir 220 before the dispensing pump 230 is operated. In at least one embodiment, the PCB assembly 250 can be configured to operate the supply pump 210 after operating the dispensing pump 230 in order to replenish the supply of fluid within the reservoir 220. In various embodiments, the PCB assembly 250 can be configured to operate the dispensing pump 230 and the supply pump 210 simultaneously such that the fluid in the reservoir 220 can be replenished as it is being dispensed by the dispensing pump 230.

As outlined above, the supply pump 210 can comprise a positive displacement pump and, in such embodiments, the PCB assembly 250 can be configured to monitor whether the supply pump 210 is delivering a correct amount of fluid to the reservoir 220 per stroke of the pump piston 212. More specifically, information regarding the fixed volumetric displacement of the supply pump 210 can be programmed within the PCB assembly 250 such that the PCB assembly 250 can evaluate whether the increase in fluid volume within the reservoir 220 per stroke of the supply pump 210, as measured by the fluid level sensor 240, matches the volumetric displacement of the supply pump 210. In the event that the increase in fluid within the reservoir 220 per stroke of the supply pump 210, as measured by the fluid level sensor 240, is equal, or at least sufficiently equal, to the fixed volumetric displacement of the supply pump 210, the PCB assembly 250 may signal to the operator of the endoscope reprocessor 100 that the supply pump 210 is being sufficiently supplied with fluid from the fluid source. In the event that the increase in fluid within the reservoir 220 per stroke of the supply pump 210, as measured by the fluid level sensor 240, is not equal, or at least sufficiently equal, to the fixed volumetric displacement of the supply pump 210, the PCB assembly 250 may signal to the operator of the endoscope reprocessor 100 that the supply pump 210 is not being sufficiently supplied with fluid from the fluid source and that the fluid source may need to be examined as the fluid source may be empty, for example. In various circumstances, examining the fluid source may include replacing or replenishing the fluid source. In various embodiments, the reservoir 220 can contain a quantity of fluid therein which can be sufficient to supply the endoscope reprocessor 100, as needed, while the operator examines the fluid supply. In previous endoscope reprocessors, the fluid circulation systems thereof drew fluid directly from the fluid supply and, thus, the endoscope reprocessor could not identify that the fluid source had been depleted until an operating cycle had already begun and the lack of fluid had interrupted the operating cycle.

In various embodiments, further to the above, the endoscope reprocessor 100 can comprise two basins 110, for example, which can each be configured such that an endoscope can be cleaned, disinfected, and/or sterilized therein. In certain embodiments, referring again to FIG. 16, the endoscope reprocessor 100 can comprise a separate fluid circulation system, such as circulation systems 290a and 290b, for example, for supplying fluid to each basin 110. In such embodiments, the fluid dispensing subsystem 200a can be configured to supply both of the fluid circulation systems 290a, 290b with fluid from fluid source 201a and, similarly, the fluid dispensing subsystem 200b can be configured to supply both of the fluid circulation systems 290a, 290b with fluid from fluid source 201b. In at least one such embodiment, the endoscope reprocessor 100 can comprise a valve 280a which can be, one, in fluid communication with the dispensing pump 230 of the fluid dispensing subsystem 200a and, two, in selective fluid communication with fluid circulation systems 290a, 290b such that a fluid can be selectively supplied to the fluid circulation systems 290a, 290b from the fluid source 201a. Similarly, the endoscope reprocessor 100 can comprise a valve 280b which can be, one, in fluid communication with the dispensing pump 230 of the fluid dispensing subsystem 200b and, two, in selective fluid communication with fluid circulation systems 290a, 290b such that a fluid can be selectively supplied to the fluid circulation systems 290a, 290b from the fluid source 201b. Prior to running an operating cycle of a fluid circulation system, in certain embodiments, the fluid circulation system may require a quantity of the fluid, such as a detergent and/or sterilant, for example, from the fluid dispensing subsystem 200a. In such embodiments, further to the above, the PCB assembly 250 can be programmed to maintain a quantity of fluid within the reservoir 220 of the subsystem 200a such that, when fluid is needed to supply a fluid circulation system 290a, 290b, the fluid is available without having to operate the supply pump 210. In various circumstances, the quantity of fluid needed from a reservoir 220 by the fluid circulation system can be larger than the volume of fluid that can be supplied by a single stroke of the dispensing pump 230 and, thus, multiple strokes of the dispensing pump 230 may be required. In any event, the quantity of a particular fluid needed by a fluid circulation system prior to an operating cycle of the instrument reprocessor 100 may equal the minimum amount of fluid that the PCB assembly 250 may be programmed to maintain in a reservoir 220. In certain embodiments, the PCB assembly 250 may be programmed to maintain enough fluid in a reservoir 220 to supply both of the fluid circulations systems with a particular fluid to begin their operating cycles without needing to be refilled by the corresponding supply pump 210. Of course, further to the above, the supply pump 210 could then be operated to refill the reservoir 220 after both of the fluid circulation systems have been supplied with a sufficient quantity of fluid. In light of the above, in various embodiments, a reservoir 220 may have enough fluid contained therein to supply at least one operating cycle of a fluid circulation system prior to the corresponding supply pump 210 being activated to refill the reservoir 220 wherein, in the event that the supply pump 210 is unable to refill the reservoir 220 due to an empty fluid supply, for example, the operator of the endoscope reprocessor 100 is afforded an opportunity to replace the fluid supply prior to the next operating cycle of a fluid circulation system.

Further to the above, the dispensing pump 230 can comprise a positive displacement pump and, in such embodiments, the PCB assembly 250 can monitor whether the dispensing pump 230 is drawing a correct amount of fluid per stroke from the reservoir 220. More specifically, information regarding the fixed volumetric displacement of the dispensing pump 230 can be programmed within the PCB assembly 250 such that the PCB assembly 250 can evaluate whether the decrease in fluid within the reservoir 220 per stroke of the dispensing pump 230, as measured by the fluid level sensor 240, matches the fixed volumetric displacement of the dispensing pump 230. In the event that the decrease in fluid within the reservoir 220 per stroke of the dispensing pump 210 is equal, or at least sufficiently equal, to the fixed volumetric displacement of the dispensing pump 230, as measured by the fluid level sensor 240, the PCB assembly 250 may signal to the operator of the endoscope reprocessor 100 that the dispensing pump 230 is being sufficiently supplied with fluid from the reservoir 220. In the event that the decrease in fluid within the reservoir 220 per stroke of the dispensing pump 230, as measured by the fluid level sensor 240, is not equal, or at least sufficiently equal, to the volumetric displacement of the dispensing pump 230, the PCB assembly 250 may signal to the operator of the endoscope reprocessor 100 that the dispensing pump 230 is not being sufficiently supplied with fluid and that some examination and/or maintenance of the fluid dispensing subsystem may be required.

As discussed above with regard to various embodiments, each fluid dispensing subsystem 200a, 200b can comprise a fluid supply pump 210 and a separate fluid dispensing pump 230. As also discussed above, in various embodiments, the fluid supply pump 210 and the fluid dispensing pump 230 can be operated independently of one another to supply fluid to and dispense fluid from the reservoir 220, respectively. In certain alternative embodiments, a single pumping apparatus can be configured to, one, pump fluid into the reservoir 220 from the fluid supply and, two, pump fluid from the reservoir 220 into a fluid circulation system. In at least one such embodiment, the pumping apparatus can comprise a piston having a first piston head positioned within a first cylinder and a second piston head positioned within a second cylinder wherein the piston can be reciprocated linearly to move the first and second piston heads within the first and second cylinders, respectively. In various embodiments, the first cylinder can be in fluid communication with a fluid source and the reservoir while the second cylinder can be in fluid communication with the reservoir and the fluid circulation system such that the first piston head moving within the first cylinder can pump fluid from the fluid source into the reservoir and the second piston head moving within the second cylinder can pump fluid from the reservoir into the fluid circulation system. In various embodiments, the arrangement of the first piston head and the first cylinder can comprise a first positive displacement pump and the arrangement of the second piston head and the second cylinder can comprise a second positive displacement pump. In certain embodiments, the pumping apparatus can comprise a valve control system which can be configured to control or limit the flow of fluid into the first cylinder and/or the second cylinder, for example. In at least one such embodiment, the valve control system can be configured to close a valve element and prevent fluid from flowing into the second cylinder while fluid is being pumped into the reservoir from the first cylinder. Similarly, the valve control system can be configured to close a valve element and prevent fluid from flowing into the first cylinder while fluid is being pumped from the reservoir through the second cylinder. In such embodiments, the first and second piston heads may be reciprocate within their respective first and second cylinders; however, the flow of fluid through of the cylinders may be prevented, as described above. In various alternative embodiments, a pump can comprise a rotary pump having a first aperture in fluid communication with the fluid source, a second aperture in fluid communication with the reservoir, and a third aperture in fluid communication with the fluid circulation system. In at least one such embodiment, a valve control system can be configured to close or block the third aperture when pumping fluid into the reservoir and, alternatively, block the first aperture when pumping fluid from the reservoir. In certain embodiments, the valve control system could include any suitable arrangement of one or more shuttle valves and/or spool valves, for example. In various embodiments, any suitable positive displacement pump including a three-way valve could be utilized to pump fluid into the reservoir 220 from a fluid source and then from the reservoir 220 into the fluid circulation system.

As discussed above, referring again to FIG. 16, the endoscope reprocessor 100 can comprise a fluid dispensing system 200 which can be configured to supply a fluid to one or more fluid circulation systems. As also discussed above, the fluid dispensing system 200 can comprise more than one fluid dispensing subsystem, such as first subsystem 200a and second subsystem 200b, for example. In various embodiments, the second subsystem 200b can be identical, or at least substantially identical, to the first subsystem 200a and, as a result, the structure and operation of the second subsystem 200b is not repeated herein for the sake of brevity. In at least one embodiment, the first subsystem 200a can be configured to dispense a first fluid to one or more fluid circulation systems, such as fluid circulation systems 290a and 290b, for example, and the second subsystem 200b can be configured to dispense a second fluid to the fluid circulation systems 290a, 290b, for example. In at least one such embodiment, the first fluid dispensing subsystem 200a can be configured to dispense a detergent, for example, to a fluid circulation system while the second fluid dispensing subsystem 200b can be configured to dispense a sterilant, such as peracetic acid, for example, to the fluid circulation system. As also discussed above, the fluid dispensing systems 200a and 200b may be operated at different times to supply the fluid circulation systems with their respective fluids at different times during the operating cycles thereof. In various other circumstances, the fluid subsystems 200a and 200b can be operated at the same time to supply the same fluid circulation system with different fluids and/or at the same time to supply different fluid circulation systems with different fluids, for example.

Further to the above, the first fluid circulation system 290a can comprise a first channel flow subsystem 160 and a first pump 162 for circulating a fluid through the first circulation system 290a while the second fluid circulation system 290b can comprise a second channel flow subsystem 160 and a second pump 160 for circulating a fluid through the second circulation system 290b. In various other embodiments, an instrument reprocessor may comprise any suitable number of fluid circulation systems; however, with regard to any one of the fluid circulation systems, the channel flow subsystem 160 thereof can be configured to control an initialization, or start-up, procedure of the fluid circulation system. More specifically, after an instrument has been placed in a basin 110 and the lid 130 has been closed, the operator can initialize an operating cycle to clean the instrument and, at such point, the channel flow subsystem 160 can be configured to control the initial flow of reprocessing fluid from the pump 162. In various embodiments, the instrument, such as an endoscope, for example, can comprise a plurality of channels, or lumens, extending therethrough which can have different lengths, diameters, and/or configurations, for example, which can cause the channels to have different overall flow resistances, or restrictions, for example. In the event that pump 162 were to be initialized with all of the proportional valves 174 in an open condition and/or the same condition, the fluid flowing from the pump 162 would tend to fill and/or pressurize the channels of the endoscope having lower flow resistances before filling and/or pressurizing the endoscope channels having higher flow resistances, for example. In various circumstances, such a situation would be transient and the desirable operating conditions or steady state operating conditions of the fluid circulation system would eventually be reached. In some circumstances, this start-up procedure is entirely suitable. In other circumstances, however, a different start-up procedure may be desirable.

In various embodiments, further to the above, the channel flow subsystem 160 can include a computer and/or a microprocessor, for example, which can arrange the valves 174 in different conditions during the initialization procedure. In at least one embodiment, the subsystem computer can operate the valves 174 to compensate for the different flow resistances, or restrictions, of the endoscope channels, for example. For instance, for the valves 174 that control the flow of fluid through the high flow resistance endoscope channels, the subsystem computer can place such valves 174 in a fully open condition while, for the valves 174 that control the flow of fluid through the low fluid resistance endoscope channels, the subsystem computer can place such valves 174 in a partially closed condition. In such embodiments, the flow of fluid from the pump 162 may tend to fill and/or pressurize all of the endoscope channels at the same time, or at least substantially the same time. In certain circumstances, the transient state for filling the channels with pressurized fluid may be shortened and a steady state operating condition, or a desirable operating condition, can be reached in less time. Such embodiments may reduce the overall time needed to run a cleaning cycle of the instrument reprocessor 100. In embodiments having eight endoscope channels and eight flow control units 170 for controlling the flow of fluid through eight corresponding channel supply lines 164, for example, the eight proportional valves 174 thereof can all be placed in different conditions, and/or the same condition, of being open, closed, partially open, and/or partially closed, for example.

In various embodiments described herein, the flow subsystem computer can utilize one or more criteria, or parameters, for controlling the valves 174 of the flow control units 170 during the initialization, or start-up, procedure. Further to the above, a first proportional valve 174 of a first control unit 170 can be configured to control the fluid flow through a first endoscope channel defined by a first value of a particular parameter, a second proportional valve 174 of a second control unit 170 can be configured to control the fluid flow through a second endoscope channel defined by a second value of the particular parameter, and a third proportional valve 174 of a third control unit 170 can be configured to control the fluid flow through a third endoscope channel defined by a third value of a particular parameter. In various embodiments, the first value of the parameter can be larger than the second value of the parameter and the second value can be larger than the third value of the parameter wherein the first valve 174 can be modulated to a first open state, the second valve 174 can be modulated to a second open state based on the difference between the first value and the second value of the parameter, and the third valve 174 can be modulated to a third open state based on the difference between the first value and the third value of the parameter in order to regulate the flow of fluid through the first, second, and third channels. In at least one such embodiment, the first open state, the second open state, and the third open state of the first, second, and third valves 174, respectively, can be selected such that, during the initialization, or start-up, procedure of the fluid circulation system, the flow of fluid through the first, second, and third endoscope channels can be evenly, or at least substantially evenly distributed, across the first, second, and third endoscope channels. In at least one embodiment, the first, second, and third open states of the valves 174 can be selected such that the volumetric flow rates through the endoscope channels are equal, or at least substantially equal, to one another as the endoscope channels fill with fluid. In such an embodiment, the fluid flow rates through the endoscope channels can increase during the initialization procedure wherein each fluid flow can increase concurrently with the other fluid flows. In at least one embodiment, the first, second, and third open states of the valves 174 can be selected such that the gauge pressure of the fluid flowing through the endoscope channels are equal, or at least substantially equal, to one another as the endoscope channels fill with fluid. In such an embodiment, the pressure or the fluid flowing through the endoscope channels can increase during the initialization procedure wherein the pressure of each fluid flow can increase concurrently with the pressure of the other fluid flows.

In at least one embodiment, further to the above, the parameter for selecting the open conditions of the proportional valves 174 can comprise the flow resistance values of the instrument channels. In various circumstances, the flow resistance value of an instrument channel can be influenced by many variables; however, the flow resistance value of an instrument channel can be largely determined by the channel length, the channel diameter, and the curves, or bends, in the channel path. Instrument channels having longer lengths, smaller diameters, and/or more curves in the channel path will typically have higher flow resistance values than instrument channels having shorter lengths, larger diameters, and/or less curves in the channel path. In any event, the instrument channel having the highest flow resistance value of the medical instrument can be selected as a baseline from which the fluid flows through the other instrument channels can be adjusted. In at least one embodiment, the first instrument channel can have the highest fluid flow resistance and the first proportional valve 174 can be set to a fully open condition, for example. In various embodiments, the second proportional valve 174 can be closed a certain amount based on the difference between the first flow resistance value and the second flow resistance value. Similarly, the third proportional valve 174 can be closed a certain amount based on the difference between the first flow resistance value and the third flow resistance value. In various circumstances, the larger the difference between the flow resistance value of an instrument channel and the first flow resistance value, or a baseline flow resistance value, the greater degree in which the corresponding proportional valve 174 can be closed.

In any event, further to the above, once the steady state operating condition, or the desirable operating condition, of the fluid circulation system has been reached, the subsystem computer can permit the flow control units 170 to independently control and govern the flow of fluid through the endoscope channel supply lines 164 as discussed above. In various circumstances, the devices and methods described herein can be designed to provide an adequate supply of reprocessing fluid to clean, disinfect, and/or sterilize an endoscope, and/or any other suitable instrument, comprising channels having different flow resistances. Further to the above, these devices and methods can be configured to supply an adequate supply of reprocessing fluid to the channels by controlling the fluid flow through each channel individually.

In various circumstances, the pump 162 can have a sufficient output to supply all of the reprocessor supply lines 164 and the endoscope channels associated therewith with an adequate supply of reprocessing fluid during the initialization of the operating cycle and throughout the operating cycle. Further to the above, the flow control units 170 can be configured to manage the fluid supplied thereto such that each reprocessor supply line 164 has a flow rate therethrough which meets or exceeds the minimum target flow rate and, thus, is not starved for fluid. In the event that the fluid flow through one or more of the reprocessor supply lines 164 is below the minimum target flow rate and the pump 162 is not operating at maximum capacity, the output of the pump 162 can be increased. In some circumstances, the gauge pressure of the reprocessing fluid exiting the pump 162 can increase above the target gauge pressure, such as 35 psig, for example, at least temporarily in order for the pump 162 to meet the supply demands of the reprocessor supply lines 164 and the endoscope channels associated therewith. In the event that the fluid flow through one or more of the reprocessor supply lines 164 is below the minimum target flow rate and the pump 162 is operating at a maximum, or near maximum, capacity, at least one booster pump could be operated to increase the flow rate and/or pressure of the reprocessing fluid entering into the manifold 166 and the reprocessor supply lines 164. In various embodiments, the at least one booster pump could be in series with pump 162 and/or in parallel with the pump 162, for example, wherein the at least one booster pump could be selectively operated to assist the pump 162.

In various embodiments discussed herein, each reprocessor supply line 164 of the channel flow subsystem 160 can comprise a proportional valve 174 configured to control a variable orifice. In various other embodiments, at least one of the reprocessor supply lines 164 can include a fixed orifice or a fixed orifice valve. In at least one embodiment, the fixed orifice valve can be positionable in either an open condition or a closed condition. In at least one such embodiment, the reprocessor supply line 164 having a fixed orifice valve can be coupled to the endoscope channel having the highest fluid flow resistance, for example, wherein the fluid flow rate through such a endoscope channel may be a function of the gauge pressure of the reprocessing fluid supplied by the pump 162. In various embodiments, the reprocessor supply lines 164 having a variable orifice controlled by a proportional valve 174, for example, can be modulated with respect to the reprocessor supply line 164 having a fixed orifice valve when the fixed orifice valve is in an open condition, for example.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An instrument reprocessor for cleaning an instrument, the instrument including a passage configured to receive a reprocessing fluid, the instrument reprocessor comprising:
a chamber configured to receive the instrument;
a pump configured to pressurize the reprocessing fluid and supply the reprocessing fluid to the passage, wherein the pump comprises an inlet and an outlet;
a gauge pressure sensor positioned to sense a gauge pressure of the reprocessing fluid flowing from the pump outlet;
a proportional valve configured to direct a portion of a fluid flow from the pump to a fluid feedback loop in fluid communication with a source of fluid for the pump based at least in part on a pressure value determined by the gauge pressure sensor; and
a flow control system, comprising:
a valve in fluid communication with the passage, wherein the valve is configured to control a flow rate of reprocessing fluid through the passage, and wherein the valve comprises an inlet and an outlet;
a pressure differential sensor configured to sense a pressure differential in the reprocessing fluid on opposite sides of a fixed orifice, wherein the pressure differential sensor is positioned upstream with respect to the valve outlet; and
a processor in signal communication with the pressure differential sensor, wherein the processor is configured to interpret the flow rate based on the pressure differential and command the valve to at least one of at least partially close and at least partially open.

2. The instrument reprocessor of claim 1, wherein the pressure differential sensor is positioned downstream with respect to the gauge pressure sensor.

3. A flow control system for use with a pressurized fluid channel, the flow control system, comprising:
a valve in fluid communication with a pressurized fluid, wherein the valve is configured to control a flow rate of the pressurized fluid through the pressurized fluid channel, and wherein the valve comprises an inlet and an outlet;
a first pressure differential sensor configured to sense a first pressure differential in the pressurized fluid on opposite sides of a first fixed orifice, wherein the first pressure differential sensor is positioned upstream with respect to the valve inlet;
a first gauge pressure sensor positioned downstream with respect to the valve outlet;
a pressure regulating device in fluid communication with the pressurized fluid channel;
a second gauge pressure sensor positioned to sense a second gauge pressure of the pressurized fluid flowing from an outlet of the pressure regulating device;
a proportional valve configured to direct a portion of fluid flow from the pressure regulating device to a fluid feedback loop in fluid communication with a source of fluid for the pressure regulating device based at least in part on a pressure value determined by the second gauge pressure sensor; and
a processor in signal communication with the first pressure differential sensor and the first gauge pressure sensor, wherein the processor is configured to interpret the flow rate based on the first pressure differential and command the valve to at least one of at least partially close and at least partially open.

4. The flow control system of claim 3, wherein the pressure regulating device comprises a pump.

5. The flow control system of claim 3, further comprising a second pressure differential sensor configured to sense a second pressure differential in the pressurized fluid on opposite sides of a second fixed orifice,
wherein the second pressure differential sensor is disposed fluidically in parallel with the first pressure differential sensor, and
wherein the second pressure differential sensor is in signal communication with the processor.

6. The flow control system of claim 5, wherein the first pressure differential sensor transmits a first voltage reading associated with the first pressure differential to the processor,
wherein the second pressure differential sensor transmits a second voltage reading associated with the second pressure differential to the processor, and
wherein the processor is configured to execute a corrective action routine when the first voltage reading differs from the second voltage reading.

7. The flow control system of claim 6, wherein the corrective action routine comprises issuing a warning to an operator of the flow control system.

8. An instrument reprocessor for cleaning a medical instrument, the medical instrument including a passage, the instrument reprocessor comprising:
a chamber configured to receive the medical instrument;
a supply connector configured to be fluidly coupled with the passage;
a pump configured to pressurize a reprocessing fluid and supply the reprocessing fluid to the supply connector, wherein the pump comprises an inlet and an outlet;
a first gauge pressure sensor positioned to sense a first gauge pressure of the reprocessing fluid flowing from the pump outlet;
a proportional valve configured to direct a portion of a fluid flow from the pump to a fluid feedback loop in fluid communication with a source of fluid for the pump based at least in part on the first gauge pressure; and
at least one flow control system, comprising:
a valve in fluid communication with the supply connector, wherein the valve is configured to control a flow rate of reprocessing fluid through the passage, and wherein the valve comprises an inlet and an outlet;
a first pressure differential sensor configured to sense a first pressure drop in the reprocessing fluid on opposite sides of a first fixed orifice, wherein the first pressure differential sensor is positioned downstream with respect to the first gauge pressure sensor and upstream with respect to the valve outlet;
a second pressure differential sensor configured to sense a second pressure drop in the reprocessing fluid on opposite sides of a second fixed orifice, wherein the second pressure differential sensor is disposed fluidcally in parallel with the first pressure differential sensor;
a second gauge pressure sensor positioned downstream with respect to the valve outlet; and
a processor in signal communication with the first pressure differential sensor, the second pressure differential sensor, and the second gauge pressure sensor, wherein the processor is configured to interpret the flow rate based on the first pressure drop and command the valve to at least one of at least partially close and at least partially open.

9. The instrument reprocessor of claim 8, wherein the processor is configured to interpret a first flow rate based on the first pressure drop and a second flow rate based on the second pressure drop, and wherein the processor is configured to execute a corrective action routine when the first flow rate differs from the second flow rate.

10. The instrument reprocessor of claim 8, wherein the at least one flow control system comprises a plurality of flow control systems.

11. The instrument reprocessor of claim 10, where at least one flow control system of the plurality of flow control systems is fluidically and electrically independent of at least a second flow control system of the plurality of flow control systems.

* * * * *